United States Patent
Dale et al.

(10) Patent No.: US 12,295,837 B2
(45) Date of Patent: May 13, 2025

(54) MITRAL HEART VALVE REPLACEMENT

(71) Applicant: St. Jude Medical, Cardiology Division, Inc., St. Paul, MN (US)

(72) Inventors: Theodore Paul Dale, Corcoran, MN (US); Katherine A. Ahmann, Arden Hills, MN (US); Brian Joseph Perszyk, Shoreview, MN (US); Mathias Charles Glimsdale, St. Michael, MN (US); Kristopher Henry Vietmeier, Monticello, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 65 days.

(21) Appl. No.: 17/936,222

(22) Filed: Sep. 28, 2022

(65) Prior Publication Data

US 2023/0090160 A1  Mar. 23, 2023

Related U.S. Application Data

(60) Division of application No. 16/409,413, filed on May 10, 2019, now abandoned, which is a continuation of
(Continued)

(51) Int. Cl.
A61F 2/24 (2006.01)

(52) U.S. Cl.
CPC .......... *A61F 2/2418* (2013.01); *A61F 2/2412* (2013.01); *A61F 2210/0014* (2013.01); *A61F 2220/0008* (2013.01); *A61F 2250/006* (2013.01)

(58) Field of Classification Search
CPC .................................................. A61F 2/2418
See application file for complete search history.

(56) References Cited

U.S. PATENT DOCUMENTS

| | | |
|---|---|---|
| 3,657,744 A | 4/1972 | Ersek |
| 4,275,469 A | 6/1981 | Gabbay |
| (Continued) | | |

FOREIGN PATENT DOCUMENTS

| | | | | |
|---|---|---|---|---|
| CN | 101953723 A | * | 1/2011 | |
| CN | 101953729 A | * | 1/2011 | ........... A61F 2/2418 |
| (Continued) | | | | |

OTHER PUBLICATIONS

"Transluminal Implantation of Artificial Heart Valves", Andersen, H. R., et al., European Heart Journal, vol. 13, No. 5, May 1992, pp. 704-708.

(Continued)

*Primary Examiner* — Jacqueline Woznicki
(74) *Attorney, Agent, or Firm* — SLEMAN & LUND LLP

(57) ABSTRACT

A prosthetic heart valve includes a collapsible and expandable stent extending along a longitudinal axis and having an inflow end and an outflow end, the stent including a plurality of cells annularly arranged around the stent in at least one row, the plurality of cells having a first nesting cell adjacent the outflow end of the stent, a first engaging arm disposed within the first nesting cell and being pivotally movable between a loaded condition, a partially-released condition, and a fully-released condition, the first engaging arm and the first nesting cell having a synchronous pivoting movement, and a collapsible and expandable valve assembly disposed within the stent and having a plurality of leaflets.

17 Claims, 18 Drawing Sheets

Related U.S. Application Data application No. 15/591,380, filed on May 10, 2017, now Pat. No. 10,299,921.

(60) Provisional application No. 62/335,294, filed on May 12, 2016.

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann |
| 4,922,905 A | 5/1990 | Strecker |
| 4,994,077 A | 2/1991 | Dobben |
| 5,411,552 A | 5/1995 | Andersen |
| 5,415,664 A | 5/1995 | Pinchuk |
| 5,480,423 A | 1/1996 | Ravenscroft |
| 5,824,053 A * | 10/1998 | Khosravi ............ A61F 2/88 623/1.14 |
| 5,843,167 A | 12/1998 | Dwyer |
| 5,855,601 A | 1/1999 | Bessler |
| 5,935,163 A | 8/1999 | Gabbay |
| 5,961,549 A | 10/1999 | Nguyen |
| 6,077,297 A | 6/2000 | Robinson |
| 6,083,257 A | 7/2000 | Taylor |
| 6,090,140 A | 7/2000 | Gabbay |
| 6,214,036 B1 | 4/2001 | Letendre |
| 6,264,691 B1 | 7/2001 | Gabbay |
| 6,267,783 B1 | 7/2001 | Letendre |
| 6,368,348 B1 | 4/2002 | Gabbay |
| 6,419,695 B1 | 7/2002 | Gabbay |
| 6,458,153 B1 | 10/2002 | Bailey |
| 6,468,660 B2 | 10/2002 | Ogle |
| 6,488,702 B1 | 12/2002 | Besselink |
| 6,517,576 B2 | 2/2003 | Gabbay |
| 6,533,810 B2 | 3/2003 | Hankh |
| 6,582,464 B2 | 6/2003 | Gabbay |
| 6,610,088 B1 | 8/2003 | Gabbay |
| 6,623,518 B2 | 9/2003 | Thompson |
| 6,685,625 B2 | 2/2004 | Gabbay |
| 6,719,789 B2 | 4/2004 | Cox |
| 6,730,118 B2 | 5/2004 | Spenser |
| 6,783,556 B1 | 8/2004 | Gabbay |
| 6,790,230 B2 | 9/2004 | Beyersdorf |
| 6,814,746 B2 | 11/2004 | Thompson |
| 6,830,584 B1 | 12/2004 | Seguin |
| 6,869,444 B2 | 3/2005 | Gabbay |
| 6,893,460 B2 | 5/2005 | Spenser |
| 6,908,481 B2 | 6/2005 | Cribier |
| 7,018,406 B2 | 3/2006 | Seguin |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik |
| 7,510,572 B2 | 3/2009 | Gabbay |
| 7,524,331 B2 | 4/2009 | Birdsall |
| RE40,816 E | 6/2009 | Taylor |
| 7,585,321 B2 | 9/2009 | Cribier |
| 7,682,390 B2 | 3/2010 | Seguin |
| 7,731,742 B2 | 6/2010 | Schlick |
| 7,803,185 B2 | 9/2010 | Gabbay |
| 7,846,203 B2 | 12/2010 | Cribier |
| 7,846,204 B2 | 12/2010 | Letac |
| 7,857,845 B2 | 12/2010 | Stacchino |
| 7,914,569 B2 | 3/2011 | Nguyen |
| D648,854 S | 11/2011 | Braido |
| D652,926 S | 1/2012 | Braido |
| D652,927 S | 1/2012 | Braido |
| D653,341 S | 1/2012 | Braido |
| D653,342 S | 1/2012 | Braido |
| D653,343 S | 1/2012 | Ness |
| 8,092,520 B2 | 1/2012 | Quadri |
| D654,169 S | 2/2012 | Braido |
| D654,170 S | 2/2012 | Braido |
| 8,163,007 B2 * | 4/2012 | Dierking ............ A61F 2/95 623/1.36 |
| D660,432 S | 5/2012 | Braido |
| D660,433 S | 5/2012 | Braido |
| D660,967 S | 5/2012 | Braido |
| 8,337,541 B2 | 12/2012 | Quadri |
| 8,403,983 B2 | 3/2013 | Quadri |
| 8,414,644 B2 | 4/2013 | Quadri |
| D684,692 S | 6/2013 | Braido |
| 8,652,203 B2 | 2/2014 | Quadri |
| 8,795,356 B2 | 8/2014 | Quadri |
| 8,840,661 B2 | 9/2014 | Manasse |
| 8,840,663 B2 | 9/2014 | Salahieh |
| 8,894,702 B2 | 11/2014 | Quadri |
| 8,911,455 B2 | 12/2014 | Quadri |
| 9,023,100 B2 | 5/2015 | Quadri |
| 9,333,073 B2 | 5/2016 | Quadri |
| 9,333,074 B2 | 5/2016 | Quadri |
| 9,339,377 B2 | 5/2016 | Quadri |
| 9,339,378 B2 | 5/2016 | Quadri |
| 9,339,379 B2 | 5/2016 | Quadri |
| 9,339,380 B2 | 5/2016 | Quadri |
| 9,433,514 B2 | 9/2016 | Quadri |
| 9,456,896 B2 | 10/2016 | Quadri |
| 9,480,560 B2 | 11/2016 | Quadri |
| 9,486,336 B2 | 11/2016 | Quadri |
| 9,585,747 B2 | 3/2017 | Quadri |
| 9,597,183 B2 | 3/2017 | Quadri |
| 9,681,951 B2 | 6/2017 | Ratz |
| 9,730,790 B2 | 8/2017 | Quadri |
| 9,730,791 B2 | 8/2017 | Ratz |
| 9,744,039 B2 | 8/2017 | Quadri |
| 9,949,827 B2 | 4/2018 | Quadri |
| 9,974,669 B2 | 5/2018 | Quadri |
| 10,004,599 B2 | 6/2018 | Rabito |
| 10,149,756 B2 | 12/2018 | Quadri |
| 10,166,097 B2 | 1/2019 | Quadri |
| 10,179,044 B2 | 1/2019 | Ratz |
| 10,350,065 B2 | 7/2019 | Quadri |
| 10,376,363 B2 | 8/2019 | Quadri |
| 10,433,957 B2 * | 10/2019 | Khouengboua ........ A61F 2/2418 |
| 10,441,412 B2 | 10/2019 | Quadri |
| 10,456,277 B2 | 10/2019 | Quadri |
| 10,583,000 B2 | 3/2020 | Ratz |
| 10,610,362 B2 | 4/2020 | Quadri |
| 10,646,334 B2 | 5/2020 | Quadri |
| 10,716,664 B2 | 7/2020 | Ratz |
| 10,779,938 B2 | 9/2020 | Quadri |
| 10,881,510 B2 | 1/2021 | Quadri |
| 10,952,849 B2 | 3/2021 | Rabito |
| 11,045,313 B2 | 6/2021 | Ratz |
| 11,141,265 B2 | 10/2021 | Quadri |
| 11,324,591 B2 | 5/2022 | Ratz |
| 11,376,119 B2 | 7/2022 | Quadri |
| 11,389,292 B2 | 7/2022 | Quadri |
| 2002/0002401 A1 * | 1/2002 | McGuckin, Jr. ...... A61F 2/2475 623/1.36 |
| 2002/0022853 A1 * | 2/2002 | Swanson ............ A61F 2/88 623/1.36 |
| 2002/0036220 A1 | 3/2002 | Gabbay |
| 2002/0123790 A1 * | 9/2002 | White ............ A61F 2/07 623/1.36 |
| 2003/0023303 A1 | 1/2003 | Palmaz |
| 2003/0050694 A1 | 3/2003 | Yang |
| 2003/0083679 A1 * | 5/2003 | Grudem ............ A61B 17/11 623/1.36 |
| 2003/0130726 A1 | 7/2003 | Thorpe |
| 2003/0199975 A1 * | 10/2003 | Gabbay ............ A61F 2/2454 623/1.14 |
| 2004/0039436 A1 * | 2/2004 | Spenser ............ A61F 2/243 623/2.14 |
| 2004/0049262 A1 | 3/2004 | Obermiller |
| 2004/0093075 A1 | 5/2004 | Kuehne |
| 2004/0210304 A1 | 10/2004 | Seguin |

(56) References Cited

U.S. PATENT DOCUMENTS

| | | |
|---|---|---|
| 2004/0260394 A1* | 12/2004 | Douk .................... A61F 2/2433 606/153 |
| 2005/0096726 A1 | 5/2005 | Sequin |
| 2005/0096731 A1* | 5/2005 | Looi ..................... A61L 31/146 435/402 |
| 2005/0137690 A1* | 6/2005 | Salahieh ............... A61F 2/2427 623/1.36 |
| 2005/0137695 A1 | 6/2005 | Salahieh |
| 2005/0137697 A1 | 6/2005 | Salahieh |
| 2005/0240200 A1 | 10/2005 | Bergheim |
| 2005/0256566 A1 | 11/2005 | Gabbay |
| 2006/0008497 A1 | 1/2006 | Gabbay |
| 2006/0058872 A1* | 3/2006 | Salahieh ............... A61F 2/2412 623/1.36 |
| 2006/0074484 A1 | 4/2006 | Huber |
| 2006/0122684 A1* | 6/2006 | Lye ........................... A61F 2/07 623/1.36 |
| 2006/0122692 A1 | 6/2006 | Gilad |
| 2006/0149360 A1 | 7/2006 | Schwammenthal |
| 2006/0173532 A1 | 8/2006 | Flagle |
| 2006/0178740 A1 | 8/2006 | Stacchino |
| 2006/0195180 A1 | 8/2006 | Kheradvar |
| 2006/0206202 A1 | 9/2006 | Bonhoeffer |
| 2006/0241744 A1 | 10/2006 | Beith |
| 2006/0241745 A1 | 10/2006 | Solem |
| 2006/0259120 A1 | 11/2006 | Vongphakdy |
| 2006/0259137 A1 | 11/2006 | Artof |
| 2006/0265056 A1* | 11/2006 | Nguyen ................ A61F 2/2412 623/2.18 |
| 2006/0276813 A1 | 12/2006 | Greenberg |
| 2007/0010876 A1 | 1/2007 | Salahieh |
| 2007/0027534 A1 | 2/2007 | Bergheim |
| 2007/0043435 A1* | 2/2007 | Seguin .................. A61F 2/2433 623/2.11 |
| 2007/0055358 A1 | 3/2007 | Krolik |
| 2007/0067029 A1 | 3/2007 | Gabbay |
| 2007/0093890 A1 | 4/2007 | Eliasen |
| 2007/0100435 A1 | 5/2007 | Case |
| 2007/0118210 A1 | 5/2007 | Pinchuk |
| 2007/0213813 A1 | 9/2007 | Von Segesser |
| 2007/0233228 A1 | 10/2007 | Eberhardt |
| 2007/0244545 A1 | 10/2007 | Birdsall |
| 2007/0244552 A1 | 10/2007 | Salahieh |
| 2007/0255395 A1* | 11/2007 | Pollock .................... A61F 2/848 623/1.1 |
| 2007/0288087 A1 | 12/2007 | Fearnot |
| 2008/0021544 A1* | 1/2008 | Majercak ................ A61F 2/848 623/1.36 |
| 2008/0021552 A1 | 1/2008 | Gabbay |
| 2008/0039934 A1 | 2/2008 | Styrc |
| 2008/0071369 A1 | 3/2008 | Tuval |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey |
| 2008/0140189 A1 | 6/2008 | Nguyen |
| 2008/0147183 A1 | 6/2008 | Styrc |
| 2008/0154355 A1 | 6/2008 | Benichou |
| 2008/0154356 A1 | 6/2008 | Obermiller |
| 2008/0215144 A1* | 9/2008 | Ryan ..................... A61F 2/2418 623/2.18 |
| 2008/0243245 A1 | 10/2008 | Thambar |
| 2008/0255660 A1* | 10/2008 | Guyenot ............... A61F 2/2418 623/2.14 |
| 2008/0255661 A1* | 10/2008 | Straubinger .......... A61F 2/2427 623/2.36 |
| 2008/0255662 A1 | 10/2008 | Stacchino |
| 2008/0262602 A1 | 10/2008 | Wilk |
| 2008/0269879 A1 | 10/2008 | Sathe |
| 2009/0005863 A1* | 1/2009 | Goetz ................... A61F 2/2418 623/2.18 |
| 2009/0112309 A1 | 4/2009 | Jaramillo |
| 2009/0138079 A1 | 5/2009 | Tuval |
| 2009/0216310 A1* | 8/2009 | Straubinger .......... A61F 2/2418 623/1.26 |
| 2009/0216312 A1* | 8/2009 | Straubinger .......... A61F 2/2418 623/1.36 |
| 2009/0306768 A1 | 12/2009 | Quadri |
| 2010/0004740 A1 | 1/2010 | Seguin |
| 2010/0036479 A1* | 2/2010 | Hill ....................... A61F 2/2418 623/1.26 |
| 2010/0036484 A1 | 2/2010 | Hariton |
| 2010/0049306 A1 | 2/2010 | House |
| 2010/0087907 A1 | 4/2010 | Lattouf |
| 2010/0131055 A1 | 5/2010 | Case |
| 2010/0168778 A1 | 7/2010 | Braido |
| 2010/0168839 A1 | 7/2010 | Braido |
| 2010/0185277 A1* | 7/2010 | Braido .................. A61F 2/2409 623/2.37 |
| 2010/0191320 A1* | 7/2010 | Straubinger .......... A61F 2/2418 623/1.26 |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau |
| 2010/0249911 A1 | 9/2010 | Alkhatib |
| 2010/0249923 A1 | 9/2010 | Alkhatib |
| 2010/0286768 A1 | 11/2010 | Alkhatib |
| 2010/0298931 A1 | 11/2010 | Quadri |
| 2011/0029072 A1 | 2/2011 | Gabbay |
| 2011/0313515 A1* | 12/2011 | Quadri .................. A61F 2/2418 623/2.22 |
| 2012/0053685 A1* | 3/2012 | Cerf ..................... A61F 2/2418 623/2.17 |
| 2012/0078347 A1* | 3/2012 | Braido ..................... A61F 2/915 623/1.26 |
| 2012/0303116 A1 | 11/2012 | Gorman, III |
| 2013/0018458 A1* | 1/2013 | Yohanan ............... A61F 2/2418 623/2.38 |
| 2013/0310928 A1 | 11/2013 | Morriss |
| 2014/0236292 A1* | 8/2014 | Braido .................. A61F 2/2418 623/2.38 |
| 2014/0277411 A1* | 9/2014 | Bortlein ................... A61F 2/243 623/2.11 |
| 2014/0330371 A1* | 11/2014 | Gloss ........................ A61F 2/07 623/2.17 |
| 2015/0142104 A1 | 5/2015 | Braido |
| 2015/0289973 A1* | 10/2015 | Braido .................. A61F 2/2418 623/2.17 |
| 2015/0327994 A1 | 11/2015 | Morriss |
| 2016/0038280 A1* | 2/2016 | Morriss ................ A61F 2/2436 623/2.18 |
| 2016/0038281 A1* | 2/2016 | Delaloye .............. A61F 2/2418 623/2.18 |
| 2016/0045165 A1* | 2/2016 | Braido .................. A61F 2/2412 623/2.1 |
| 2016/0228244 A1* | 8/2016 | Cerf ..................... A61F 2/2418 |
| 2016/0278922 A1* | 9/2016 | Braido .................. A61F 2/2418 |
| 2017/0165053 A1* | 6/2017 | Buesseler ............. A61F 2/2418 |
| 2017/0165054 A1* | 6/2017 | Benson ................ A61F 2/2418 |
| 2017/0216023 A1* | 8/2017 | Lane .................... A61F 2/2409 |
| 2017/0325945 A1* | 11/2017 | Dale .................... A61F 2/2412 |
| 2018/0256327 A1* | 9/2018 | Perszyk ............... A61F 2/2436 |
| 2019/0183639 A1* | 6/2019 | Moore ................. A61F 2/2409 |
| 2020/0093616 A1 | 3/2020 | Quadri |
| 2020/0113683 A1* | 4/2020 | Dale .................... A61F 2/2418 |
| 2020/0261223 A1 | 8/2020 | Quadri |
| 2020/0337838 A1 | 10/2020 | Ratz |
| 2020/0360136 A1 | 11/2020 | Quadri |
| 2021/0113331 A1 | 4/2021 | Quadri |
| 2021/0205083 A1 | 7/2021 | Rabito |
| 2021/0315692 A1 | 10/2021 | Ratz |
| 2022/0023039 A1 | 1/2022 | Quadri |
| 2022/0249225 A1 | 8/2022 | Ratz |
| 2022/0323207 A1 | 10/2022 | Quadri |
| 2022/0331102 A1 | 10/2022 | Quadri |

(56) References Cited

U.S. PATENT DOCUMENTS

| | | | | |
|---|---|---|---|---|
| 2023/0240842 A1* | 8/2023 | Licht | ................... | A61F 2/2418 623/2.18 |
| 2024/0081985 A1* | 3/2024 | Miller | ................... | A61F 2/2418 |

FOREIGN PATENT DOCUMENTS

| | | | |
|---|---|---|---|
| DE | 19857887 B4 | 5/2005 | |
| DE | 10121210 B4 | 11/2005 | |
| DE | 102005003632 A1 | 8/2006 | |
| DE | 202008009610 U1 | 12/2008 | |
| EP | 0850607 A1 | 7/1998 | |
| EP | 1000590 A1 | 5/2000 | |
| EP | 1584306 A1 | 10/2005 | |
| EP | 1598031 A2 | 11/2005 | |
| EP | 1360942 B1 | 12/2005 | |
| EP | 1926455 A2 | 6/2008 | |
| FR | 2850008 A1 | 7/2004 | |
| FR | 2847800 B1 | 10/2005 | |
| WO | 9117720 A1 | 11/1991 | |
| WO | 9716133 A1 | 5/1997 | |
| WO | 9832412 A2 | 7/1998 | |
| WO | 9913801 A1 | 3/1999 | |
| WO | 2001028459 A1 | 4/2001 | |
| WO | 0149213 A2 | 7/2001 | |
| WO | 0156500 A2 | 8/2001 | |
| WO | 2001054625 A1 | 8/2001 | |
| WO | 2001076510 A2 | 10/2001 | |
| WO | 2002036048 A1 | 5/2002 | |
| WO | 0247575 A2 | 6/2002 | |
| WO | 02067782 A2 | 9/2002 | |
| WO | 2003047468 A1 | 6/2003 | |
| WO | 2005070343 A1 | 8/2005 | |
| WO | 2006073626 A2 | 7/2006 | |
| WO | 2007071436 A2 | 6/2007 | |
| WO | 2008070797 A2 | 6/2008 | |
| WO | 2010008548 A2 | 1/2010 | |
| WO | 2010008549 A1 | 1/2010 | |
| WO | 2010096176 A1 | 8/2010 | |
| WO | 2010098857 A1 | 9/2010 | |
| WO | WO-2011002996 A2 * | 1/2011 | ........... A61F 2/2415 |
| WO | WO-2013175468 A2 * | 11/2013 | ........... A61F 2/2418 |
| WO | 2015128747 A2 | 9/2015 | |
| WO | 2015175524 A1 | 11/2015 | |

OTHER PUBLICATIONS

Andersen, Henning Rud, Transluminal Catheter Implanted Prosthetic Heart Valves, International Journal of Angiology 7:102-106 (1998).

Braido, et al., U.S. Appl. No. 29/375,243, filed Sep. 20, 2010, titled "Surgical Stent Assembly".

Dewey, et al., "Transapical Aortic Valve Implantation: An Animal Feasibility Study", The Annals of Thoracic Surgery, vol. 82, No. 1, Jul. 2006, pp. 110-116.

Hijazi et al., Transcatheter Valve Repair, CRC Press, Jan. 2006, pp. 165-186.

International Search Report for Application No. PCT/US2017/031848 dated Aug. 3, 2017, 5 pages.

Knudsen LL, Andersen HR, Hasenkam JM. Catheter-Implanted Prosthetic Heart Valves: Transluminal catheter Implantation of a new expandable artificial heart valve in the descending thoracic aorta in isolated vessels and closed chest pigs. The International Journal of Artificial Organs. May 1993;16(5):253-62.

Mack, "Minimally invasive cardiac surgery", Surgical Endoscopy, 2006, 20:S488-S492, DOI: 10.1007/s00464-006-0110-8, presented Apr. 24, 2006.

Moazami et al., "Transluminal Aortic Valve Placement: A Feasibility Study With a Newly designed Collapsible Aortic Valve.", ASAIO Journal, (Sep. 00, 1996), vol. 42, pp. M381-M385, XP000683605.

Quaden et al., "Percutaneous aortic valve replacement: resection before implantation", European J. of Cardio-thoracic Surgery, vol. 27, Issue 5, pp. 836-840, May 2005.

Samuel V. Lichtenstein et al., Transapical Transcatheter Aortic Valve Implantation in Humans, Circulation, Jul. 2006, pp. 591-596, vol. 114.

Samuel V. Lichtenstein, "Closed heart surgery: Back to the future", The Journal of Thoracic and Cardiovascular Surgery, vol. 131, No. 5, pp. 941-943, May 2006.

TH. Walther et al., "Transapical Approach for Sutureless Stent-Fixed Aortic Valve Implantation: Experimental Results", European Journal of Cardio-Thoracic Surgery, vol. 29, No. 5, May 2006, pp. 703-708.

Webb et al., "Percutaneous Aortic Valve Implantation Retrograde From the Femoral Artery", Circulation, published online Feb. 2006, pp. 842-850, vol. 113, American Heart Association, Dallas, TX, USA.

Zegdi, Rachid, MD, PhD et al., "Is It Reasonable to Treat All Calcified Stenotic Aortic Valves With a Valved Stent?" 579-584, J. of the American College of Cardiology, vol. 51. No. 5, Feb. 5, 2008.

* cited by examiner

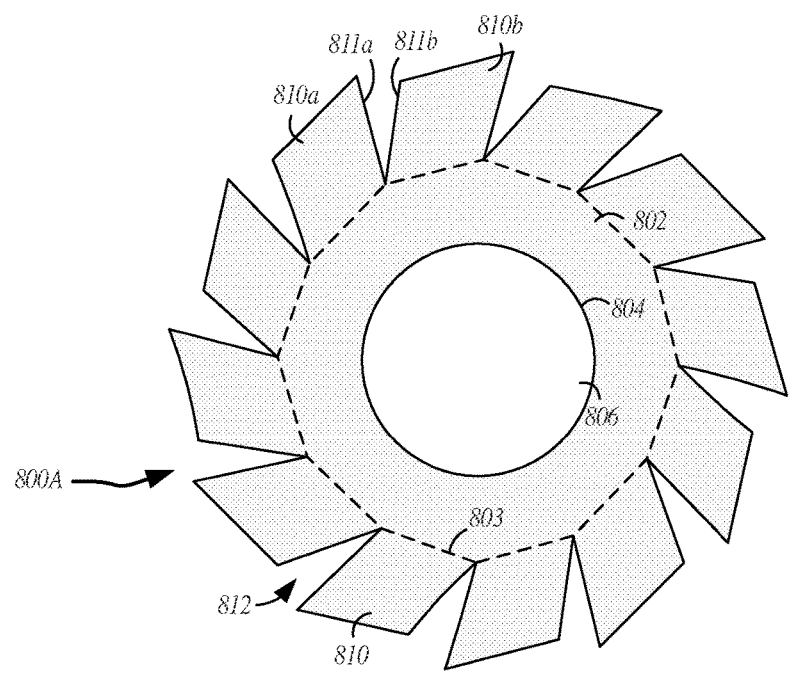
FIG. 8A
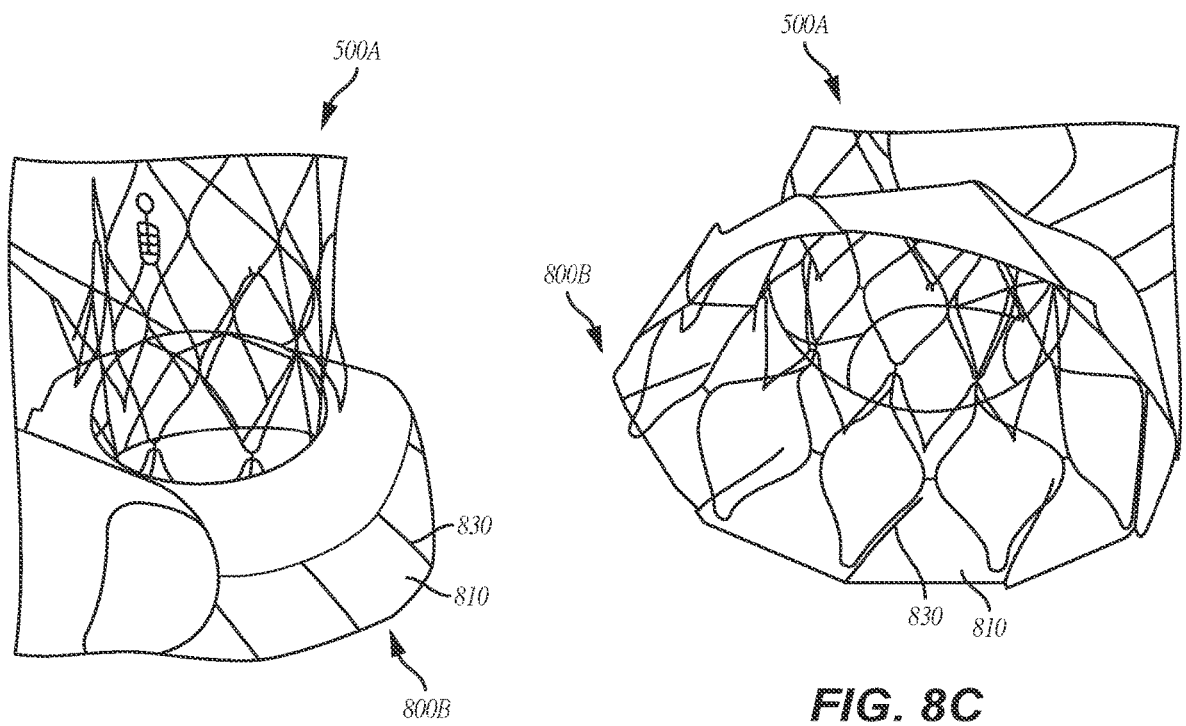
FIG. 8B
FIG. 8C

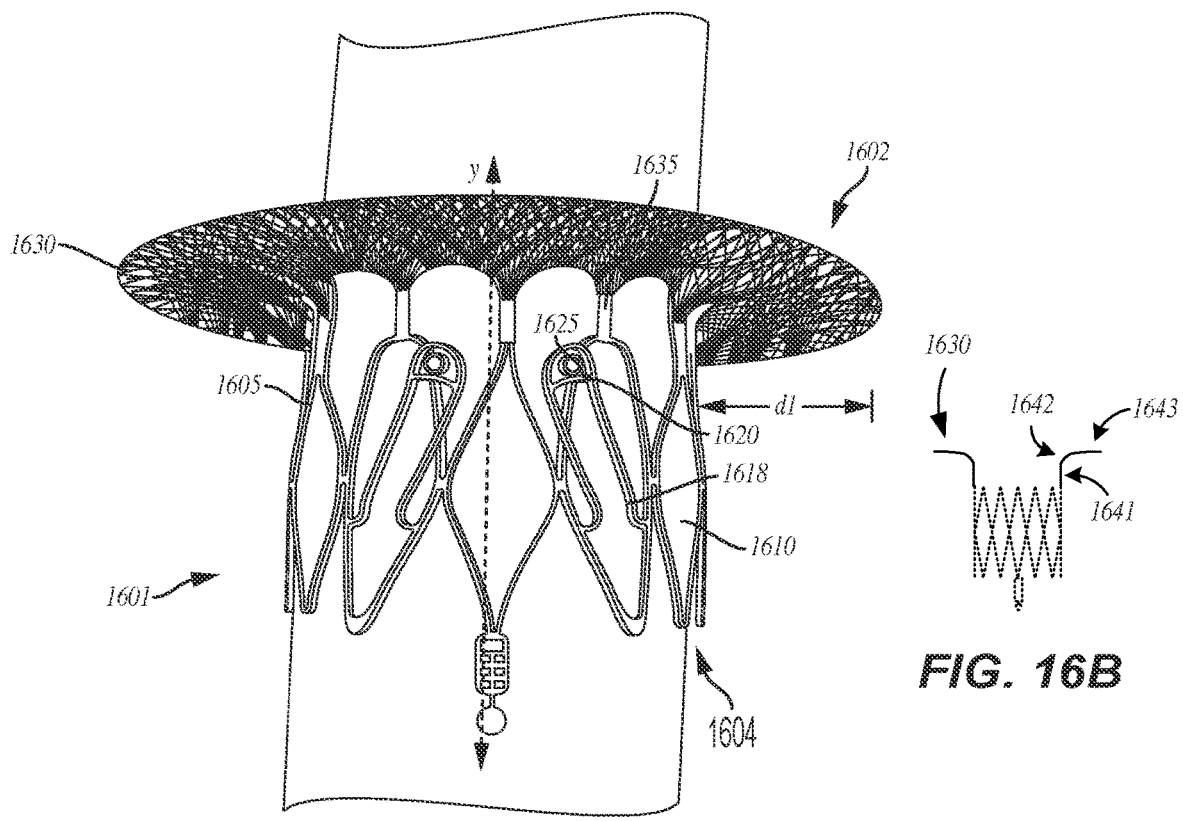
FIG. 16A
FIG. 16B
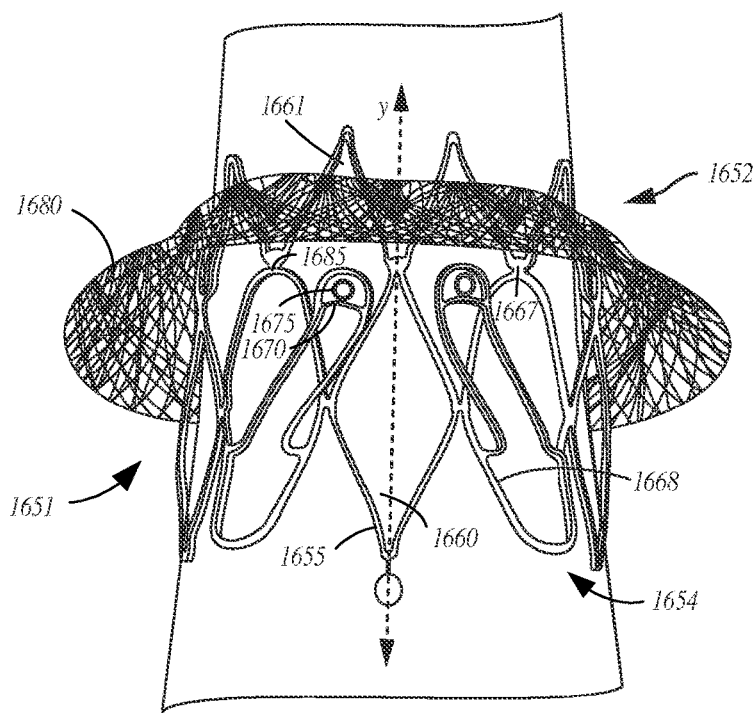
FIG. 16C
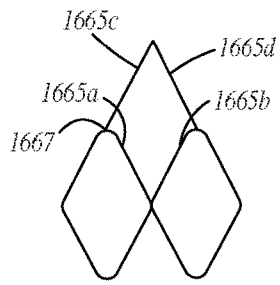
FIG. 16D
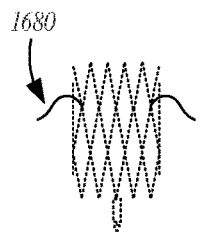
FIG. 16E

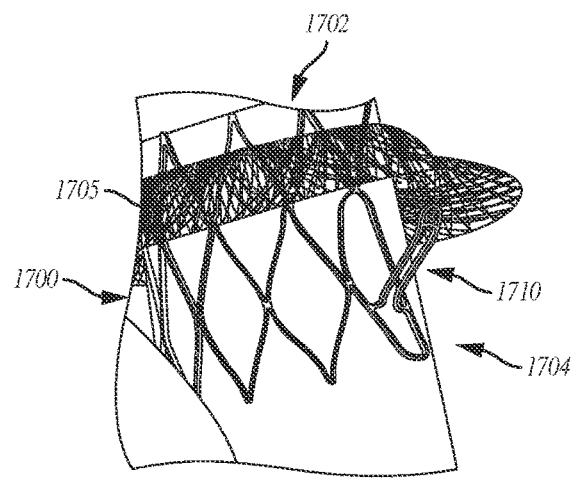
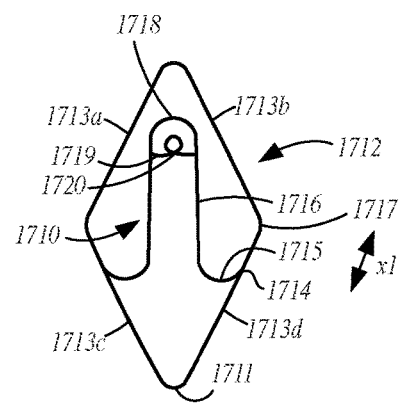
FIG. 17A  FIG. 17B
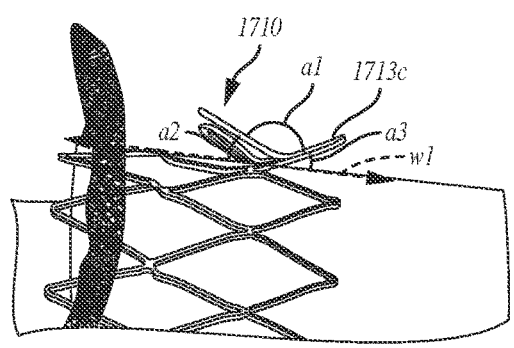
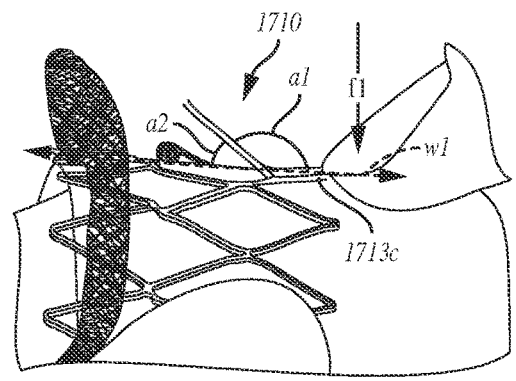
FIG. 17C  FIG. 17D
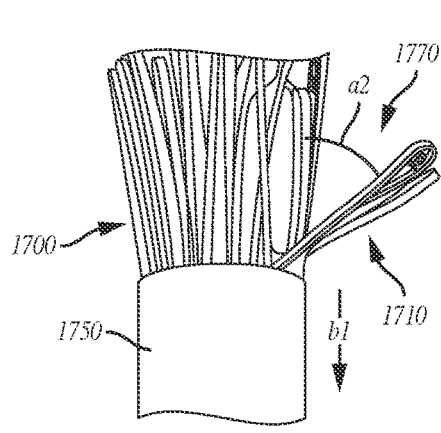
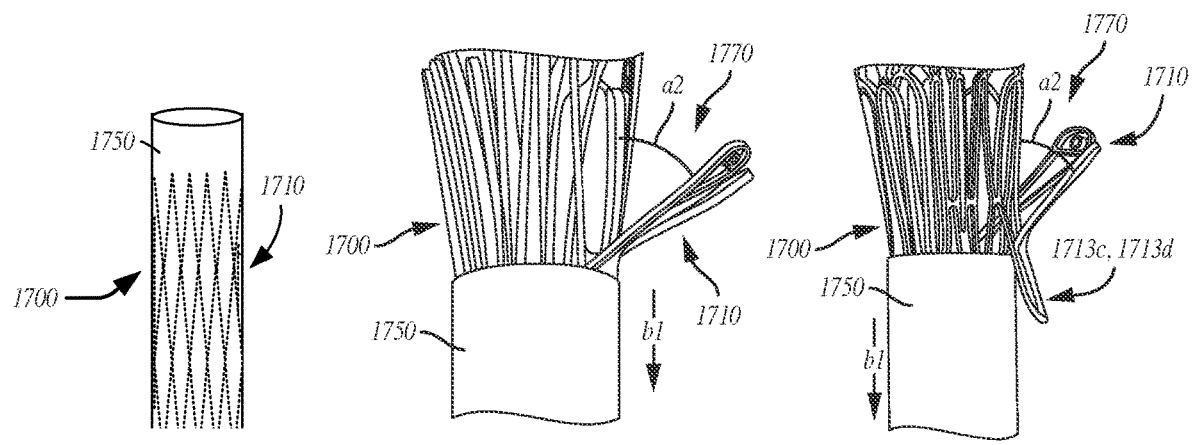
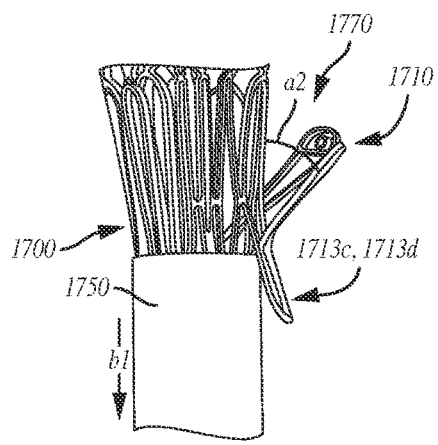
FIG. 17E  FIG. 17F  FIG. 17G

MITRAL HEART VALVE REPLACEMENT

CROSS-REFERENCE TO RELATED APPLICATIONS

This application is a divisional of U.S. application Ser. No. 16/409,413, filed May 10, 2019, which is a continuation of U.S. application Ser. No. 15/591,380, filed on May 10, 2017, and claims the benefit of the filing date of U.S. Provisional Patent Application No. 62/335,294 filed May 12, 2016, the disclosures of which are hereby incorporated herein by reference.

BACKGROUND OF THE INVENTION

The present disclosure relates to heart valve replacement and, in particular, to collapsible prosthetic heart valves. More particularly, the present disclosure relates to devices and methods for replacing the functionality of a native mitral valve.

Diseased and/or defective heart valves may lead to serious health complications. One method of addressing this condition is to replace a non-functioning heart valve with a prosthetic valve. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve has an inflow end, an outflow end and a longitudinal axis extending from the inflow end to the outflow end and includes a collapsible and expandable stent including a plurality of cells arranged in at least one row extending around a circumference of the stent. The stent further includes at least one engaging arm joined to one of the cells adjacent the outflow end and having a free end extending toward the inflow end, the engaging arm being movable between a loaded condition in which the engaging arm is oriented substantially parallel with the longitudinal axis of the stent, a partially-released condition in which the engaging arm forms a first angle with the longitudinal axis of the stent, and a fully-released condition in which the engaging arm forms a second angle with the longitudinal axis of the stent, the first angle being larger than the second angle. A collapsible and expandable valve assembly is disposed within the stent and having a plurality of leaflets.

In some embodiments, a prosthetic heart valve has an inflow end and an outflow end, and may include a collapsible and expandable stent including a plurality of cells arranged in at least one row extending around a circumference of the stent. The stent further includes at least one engaging arm joined to one of the cells adjacent the outflow end and having a free end extending toward the inflow end, the engaging arm being connected to a selected cell, the one cell having two upper struts joined to one another at an upper apex, two lower struts joined one another at a lower apex, the lower struts being joined to the upper struts at corners, the engaging arm being joined to the lower struts of the one cell and movable between a loaded condition and a relaxed condition, the engaging arm being sloped with respect to a longitudinal axis of the one cell in the relaxed condition. A collapsible and expandable valve assembly may be disposed within the stent and having a plurality of leaflets.

In some embodiments, a method of delivering a prosthetic heart valve may include providing a collapsible and expandable valve assembly and a collapsible and expandable stent having an inflow end, an outflow end, and a longitudinal axis extending from the inflow end to the outflow end, the stent including a plurality of cells arranged in at least one row, each row extending around a circumference of the stent, the stent further including at least one engaging arm joined to one of the cells adjacent the outflow end and having a free end extending toward the inflow end, the one cell having two upper struts joined to one another at an upper apex, two lower struts joined one another at a lower apex, the lower struts being joined to the upper struts at corners, the engaging arm being joined to the lower struts of the one cell. The stent and valve assembly may be loaded within a delivery sheath, and the delivery sheath may be advanced to a patient's native valve annulus.

BRIEF DESCRIPTION OF THE DRAWINGS

Various embodiments of the present disclosure are disclosed herein with reference to the drawings, wherein:

FIG. 8A is a highly schematic top view of a skirt for a prosthetic heart valve;

FIG. 8B is a top perspective view of a prosthetic heart valve stent having the skirt of FIG. 8A;

FIG. 8C is a bottom perspective view of a prosthetic heart valve stent having the skirt of FIG. 8B;

FIGS. 16A-B are a photograph and a schematic representation of the profile of a variation of a prosthetic heart valve having a braided crown;

FIGS. 16C-E are a photograph and schematic representations of the profile of a variation of a prosthetic heart valve having another example of a braided crown;

FIGS. 17A-G are photographs and schematic representations a variation of a stent having teeter-totter engaging arms.

Various embodiments of the present disclosure will now be described with reference to the appended drawings. It is to be appreciated that these drawings depict only some embodiments of the disclosure and are therefore not to be considered limiting of its scope.

DETAILED DESCRIPTION

In conventional collapsible prosthetic heart valves, the stent is usually anchored within the native valve annulus via radial forces exerted by the expanding stent against the native valve annulus. If the radial force is too high, damage may occur to heart tissue. If, instead, the radial force is too low, the heart valve may move from its implanted position, for example, into the left ventricle. Because such anchoring partly depends on the presence of calcification or plaque in the native valve annulus, it may be difficult to properly anchor the valve in locations where plaque is lacking (e.g., the mitral valve annulus). Additionally, in certain situations it may be preferable to restore native valve leaflet function rather than implanting a prosthetic device to replace that function.

In view of the foregoing, there is a need for further improvements to the devices, systems, and methods for replacing the function of a native heart valve, such as a mitral valve, a tricuspid valve, an aortic valve, or a pulmonary valve. Among other advantages, the present disclosure may address one or more of these needs. While many of the examples are described herein with reference to a specific valve (e.g., a mitral valve or a tricuspid valve), it will be understood that many of these examples are not so limited and that the concepts described apply equally to other heart valves unless expressly limited herein.

Blood flows through the mitral valve from the left atrium to the left ventricle. As used herein, the term "inflow," when used in connection with a prosthetic mitral heart valve, refers to the end of the heart valve closest to the left atrium when the heart valve is implanted in a patient, whereas the term "outflow," when used in connection with a prosthetic mitral heart valve, refers to the end of the heart valve closest to the left ventricle when the heart valve is implanted in a patient. When used in connection with a prosthetic aortic valve, "inflow" refers to the end closest to the left ventricle and "outflow" refers to the end closest to the aorta. The same convention is applicable for other valves wherein "inflow" and "outflow" are defined by the direction of blood flow therethrough. Also, as used herein, the words "substantially," "approximately," "generally" and "about" are intended to mean that slight variations from absolute are included within the scope of the structure or process recited.

Figure 1:
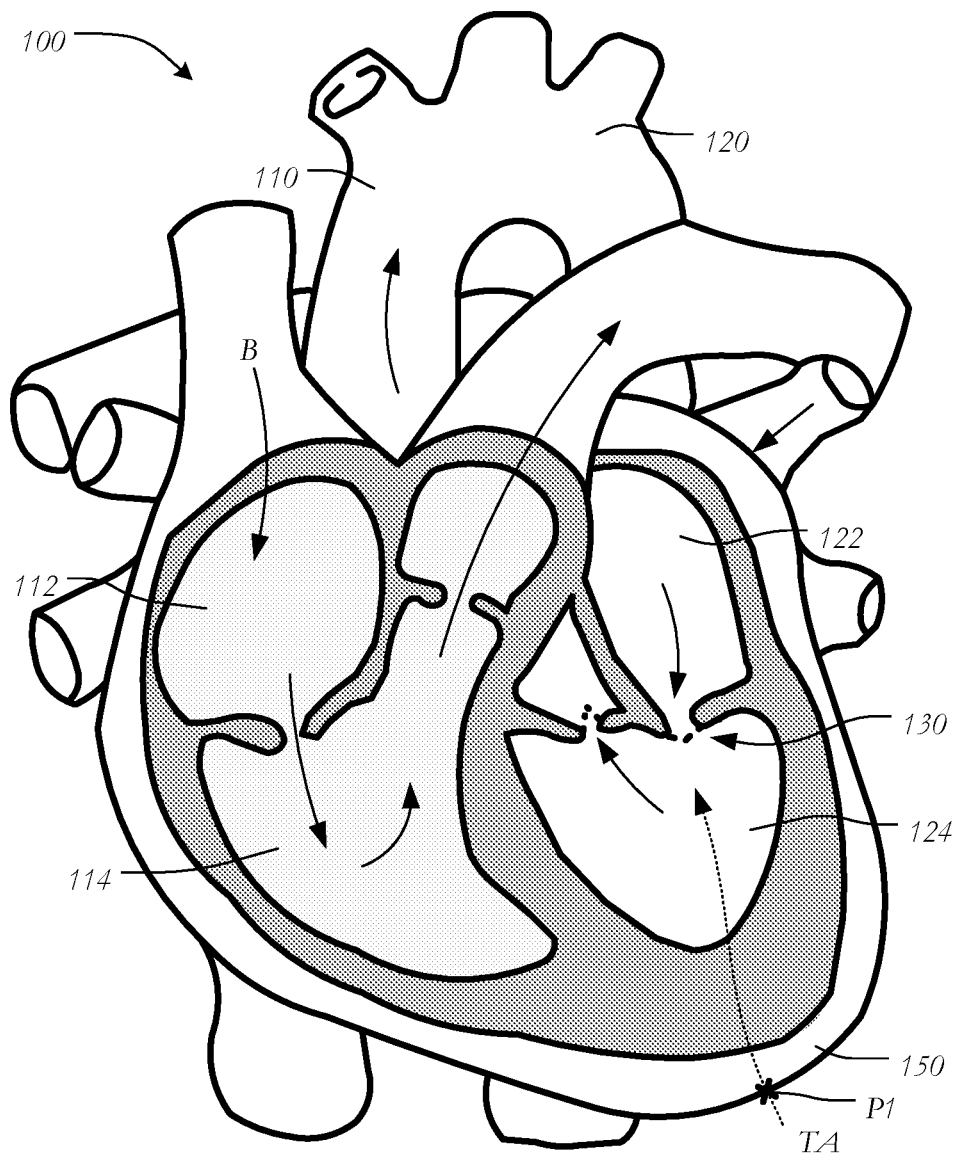
FIG. 1 is a schematic representation of a human heart showing a transapical delivery approach.

FIG. 1 is a schematic representation of a human heart 100. The human heart includes two atria and two ventricles: a right atrium 112 and a left atrium 122, and a right ventricle 114 and a left ventricle 124. As illustrated in FIG. 1, the heart 100 further includes an aorta 110, and an aortic arch 120. Disposed between the left atrium and the left ventricle is the mitral valve 130. The mitral valve 130, also known as the bicuspid valve or left atrioventricular valve, is a dual-flap that opens as a result of increased pressure in the left atrium as it fills with blood. As atrial pressure increases above that of the left ventricle, the mitral valve opens and blood passes toward the left ventricle. Blood flows through heart 100 in the direction shown by arrows "B".

A dashed arrow, labeled "TA", indicates a transapical approach for repairing or replacing heart valves, such as a mitral valve. In transapical delivery, a small incision is made between the ribs and into the apex of the left ventricle 124 at position "P1" in heart wall 150 to deliver a prosthesis or device to the target site.

Figure 2A:
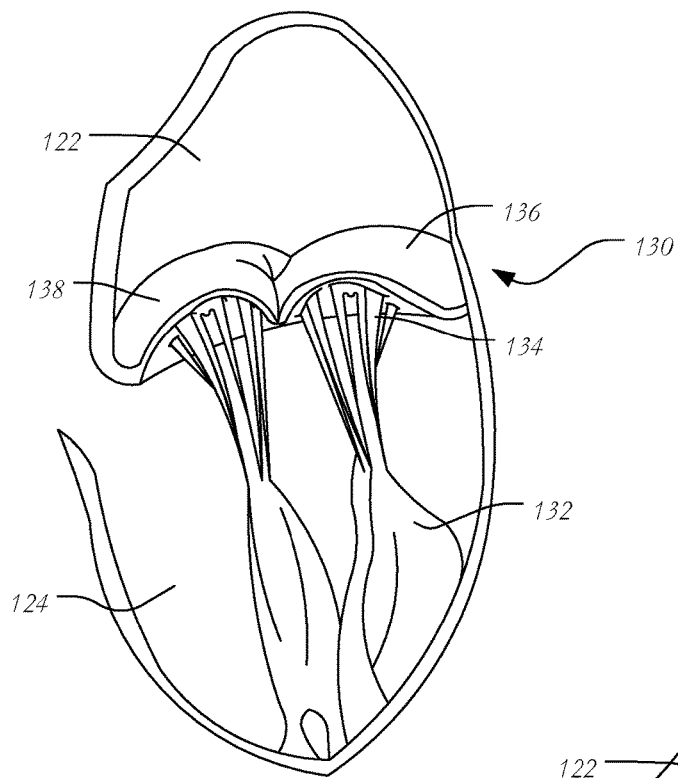
FIG. 2A is a schematic representation of a native mitral valve and associated structures during normal operation.

FIG. 2A is a more detailed schematic representation of a native mitral valve 130 and its associated structures. Mitral valve 130 includes two flaps or leaflets, a posterior leaflet 136 and an anterior leaflet 138, disposed between left atrium 122 and left ventricle 124. Cord-like tendons known as chordae tendineae 134 connect the two leaflets 136, 138 to the medial and lateral papillary muscles 132. During atrial systole, blood flows from the left atrium to the left ventricle down the pressure gradient. When the left ventricle contracts in ventricular systole, the increased blood pressure in the chamber pushes the mitral valve to close, preventing backflow of blood into the left atrium. Since the blood pressure in the left atrium is much lower than that in the left ventricle, the flaps attempt to evert to the low pressure regions. The chordae tendineae prevent the eversion by becoming tense, thus pulling the flaps and holding them in the closed position.

Figure 2B:
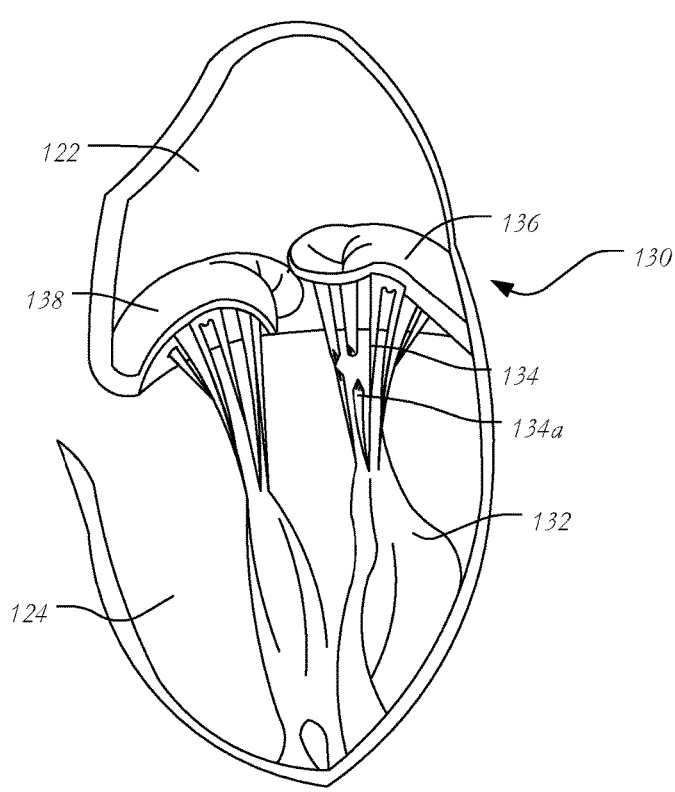
FIG. 2B is a schematic representation of a native mitral valve having a prolapsed leaflet.

FIG. 2B is a schematic representation of a prolapsed mitral valve. Posterior leaflet 136 has prolapsed into left atrium 122. Moreover, certain chordae tendineae have stretched and others have ruptured. Because of damaged chordae 134a, even if posterior leaflet 136 returns to its intended position, it will eventually resume the prolapsed position due to being inadequately secured. Thus, mitral valve 130 is incapable of functioning properly and blood is allowed to return to the left atrium and the lungs. It will be understood that, in addition to chordae damage, other abnormalities or failures may be responsible for mitral valve insufficiency.

Figure 3:
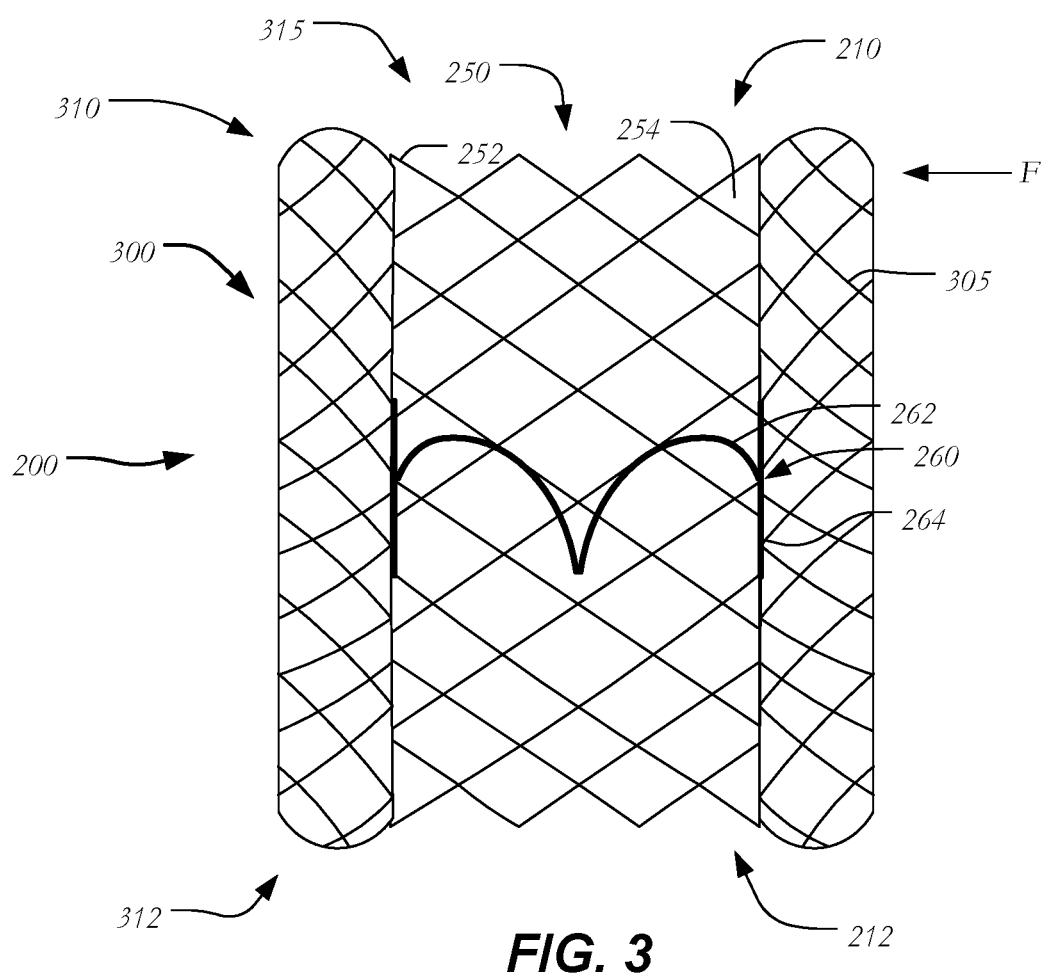
FIG. 3 is a schematic longitudinal cross-section of one embodiment of a prosthetic heart valve having a stent, a valve assembly, and a frame.

FIG. 3 is a longitudinal cross-section of prosthetic heart valve 200 in accordance with one embodiment of the present disclosure. Prosthetic heart valve 200 is a collapsible prosthetic heart valve designed to replace the function of the native mitral valve of a patient (see native mitral valve 130 of FIGS. 1-2). Generally, prosthetic valve 200 has inflow end 210 and outflow end 212. Prosthetic valve 200 may be substantially cylindrically shaped and may include features for anchoring, as will be discussed in more detail below. When used to replace native mitral valve 130, prosthetic valve 200 may have a low profile so as not to interfere with atrial function.

Prosthetic heart valve 200 includes stent 250, which may be formed from biocompatible materials that are capable of self-expansion, such as, for example, shape memory alloys including Nitinol. Alternatively, stent 250 may be formed of a material suitable for balloon-expansion. In one example, stent 250 is formed by laser cutting a predetermined pattern into a metallic tube. Stent 250 may include a plurality of struts 252 that form cells 254 connected to one another in one or more annular rows around the stent. Cells 254 may all be of substantially the same size around the perimeter and along the length of stent 250. Alternatively, cells 254 near inflow end 210 may be larger than the cells near outflow end 212. Stent 250 may be expandable to provide a radial force to assist with positioning and stabilizing prosthetic heart valve 200 within the native mitral valve annulus.

Prosthetic heart valve 200 may also include valve assembly 260, including a pair of leaflets 262 attached to a cylindrical cuff 264. Leaflets 262 replace the function of native mitral valve leaflets 136 and 138 described above with reference to FIG. 2. That is, leaflets 262 coapt with one another to function as a one-way valve. It will be appreciated, however, that prosthetic heart valve 200 may have more than two leaflets when used to replace a mitral valve or other cardiac valves within a patient. Valve assembly 260 of prosthetic heart valve 200 may be substantially cylindrical, or may taper outwardly from outflow end 212 to inflow end 210. Both cuff 264 and leaflets 262 may be wholly or partly formed of any suitable biological material, such as bovine or porcine pericardium, or polymers, such as PTFE, urethanes and the like.

When used to replace a native mitral valve, valve assembly 260 may be sized in the range of about 20 mm to about 40 mm in diameter. Valve assembly 260 may be secured to stent 250 by suturing to struts 252 or by using tissue glue, ultrasonic welding or other suitable methods.

An optional frame 300 may surround and house valve assembly 260 and stent 250. Frame 300 may be formed of a braided material in various configurations to create shapes and/or geometries for engaging tissue and filling the spaces between valve assembly 260 and the native valve annulus. As shown in FIG. 3, frame 300 includes a plurality of braided strands or wires 305 arranged in three-dimensional shapes. In one example, wires 305 form a braided metal fabric that is both resilient and capable of heat treatment substantially to a desired preset shape. One class of materials which meets these qualifications is shape memory alloys. One example of a suitable shape memory alloy is Nitinol. It is also contemplated that wires 305 may comprise various materials other than Nitinol that have elastic and/or memory properties, such as spring stainless steel, alloys such as Elgiloy®, Hastelloy®, and MP35N®, CoCrNi alloys (e.g., trade name Phynox), CoCrMo alloys, or a mixture of metal and polymer fibers. Depending on the individual material selected, the strand diameter, number of strands, and pitch may be altered to achieve desired properties for frame 300.

In the simplest configuration of frame 300, shown in FIG. 3, frame 300 may be formed in a cylindrical or tubular configuration having inlet end 310, outlet end 312 and lumen 315 extending between inlet end 310 and outlet end 312 for housing stent 250 and valve assembly 260. However, in certain embodiments stent 250 may be omitted, and valve assembly 260 may be directly attached to frame 300 using any of the techniques described above for attaching valve assembly 260 to stent 250. Frame 300 may be radially collapsed from a relaxed or preset configuration to a compressed or reduced configuration for delivery into the patient. Once released after delivery, the shape-memory properties of frame 300 may cause it to re-expand to its relaxed or preset configuration. Frame 300 may also be locally compliant in a radial direction such that a force exerted in the direction of arrow F deforms a portion of the frame. In this manner, irregularities in the native valve annulus may be filled by frame 300, thereby preventing paravalvular leakage. Moreover, portions of frame 300 may endothelialize and in-grow into the heart wall over time, providing permanent stability and a low thrombus surface.

Figure 4:
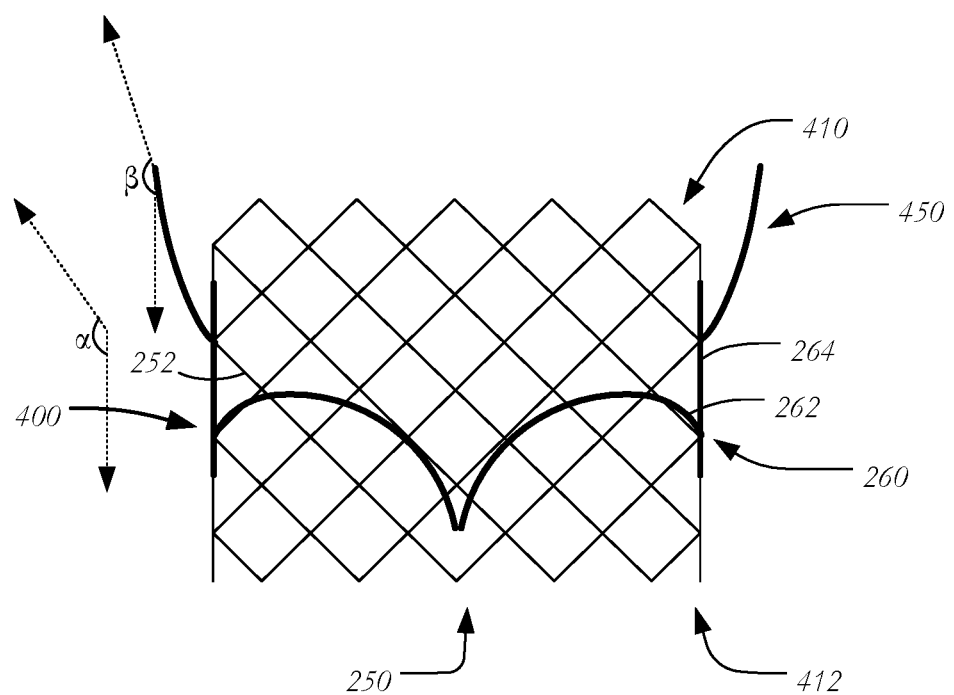
FIG. 4 is a schematic longitudinal cross-section of one embodiment of a prosthetic heart valve having a stent, a valve assembly, and a flared portion.

FIG. 4 illustrates one variation in which prosthetic heart valve 400 includes additional features to aid in fixing the valve at a predetermined location within the native valve annulus. Prosthetic heart valve 400 generally extends between inflow end 410 and outflow end 412 and includes all of the elements disclosed above including stent 250 formed of struts 252, and valve assembly 260 having leaflets 262 and cuff 264. Stent 250 may be substantially cylindrical and may further include flared portion 450 adjacent inflow end 410 that projects radially outward from the cylindrical stent to anchor the stent at a predetermined location in the native valve annulus. Flared portion 450 forms an angle α with the longitudinal axis of stent 250. In some examples, angle α may be between about 80 degrees and about 180 degrees. In some examples, angle α may be between about 90 and 110 degrees. Moreover, as shown in FIG. 4, flared portion 450 may be curved. Thus, flared portion 450 may have an initial takeoff angle α and then round out along its length to form a second angle β with the longitudinal axis of stent 250 near its distal end. As a result of the rounding, second angle β may be between about 160 degrees and about 180 degrees. During delivery, flared portion 450 may be compressed against the outside of collapsed stent 250 within a sheath of a delivery device and may return to its flared configuration when released from the sheath. When prosthetic heart valve 400 is used to replace the function of a native mitral valve, flared portion 450 may be disposed at least partially within the left atrium. Details of flared portion 450 are explored further below with reference to FIGS. 5A and 5B.

Figure 5A:
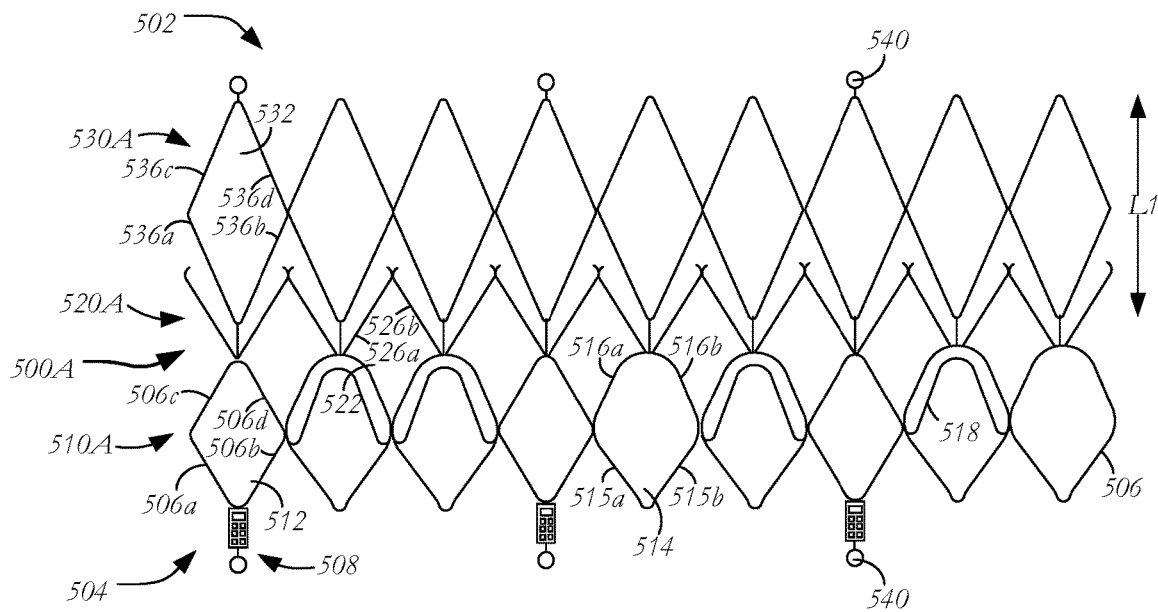
FIG. 5A is a developed view of one example of a stent having a flared portion and a plurality of engaging arms.

FIG. 5A is a developed view of a stent 500A suitable for use in a mitral heart valve prosthesis. Stent 500A generally extends in a length direction between inflow end 502 and outflow end 504 and includes a plurality of struts 506 forming rows of cells 510A, 520A, 530A, and a plurality of commissure features 508. First row of cells 510A is disposed adjacent outflow end 504 and includes symmetric cells 512, typically disposed adjacent commissure features 508, and asymmetric cells 514 at selected positions within first row 510A. Symmetric cells 512 may be substantially diamond-shaped and include four substantially straight struts 506a-d of substantially equal length. Asymmetric cells 514 may include a pair of substantially straight struts 515a, 515b which form a V-shape attached to substantially curved struts 516a, 516b. Nested within selected ones of asymmetric cells 514 are engaging arms 518, which extend generally from the connection of one cell 514 to the adjacent cells on either side thereof in row 510A. Engaging arms 518 have a curved shape which generally follows the curved shape of struts 516a, 516b, and may be configured to engage portions of heart tissue (e.g., native valve leaflets) by contacting, clasping, gripping, or securing to the tissue or otherwise preventing, minimizing or limiting the movement of stent 500A when the stent is deployed in a patient as part of a prosthetic heart valve. Second row of cells 520A may include a plurality of cells 522 formed by two struts shared with cells from first row 510A (e.g., struts 506c, 506d, 516a, 516b) and two substantially straight struts 526a, 526b. A third row of cells 530A includes enlarged cells 532 formed of struts 536a-d, each of which is longer than struts 506a-d. Third row 530A may include cells that have a length L1 that is greater than the lengths of other cells. In at least some examples, length L1 may be between about 20 mm and about 30 mm. Third row 530A of enlarged cells 532 may be configured to form a diameter greater than the diameter formed by the first two rows. Thus, as shown in the cross-sectional schematic of FIG. 4, when stent 500A fully expands, third row 530A of enlarged cells 532 forms a flared portion. Optionally, a number of retainers 540 may be disposed on selected enlarged cells 532 as well as on commissure features 508 to help hold stent 500A in the delivery apparatus and aid in its deployment.

As shown in FIG. 5A, stent 500A is formed of three rows of cells, each row having nine cells and is thus referred to as a nine-cell configuration. As briefly discussed, engaging arms 518 are nested within selected asymmetric cells 514 to engage the native valve leaflets. Because the native mitral valve includes two native leaflets, the illustrated example includes two engaging arms 518 for mating with each native valve leaflet, the first pair of engaging arms being spaced apart from the second pair of engaging arms so that they are approximately contralateral to one another. It will be understood, however, that in a nine-cell stent configuration, it may be difficult to provide pairs of engaging arms that are exactly 180 degrees apart from one another.

Figure 5B:
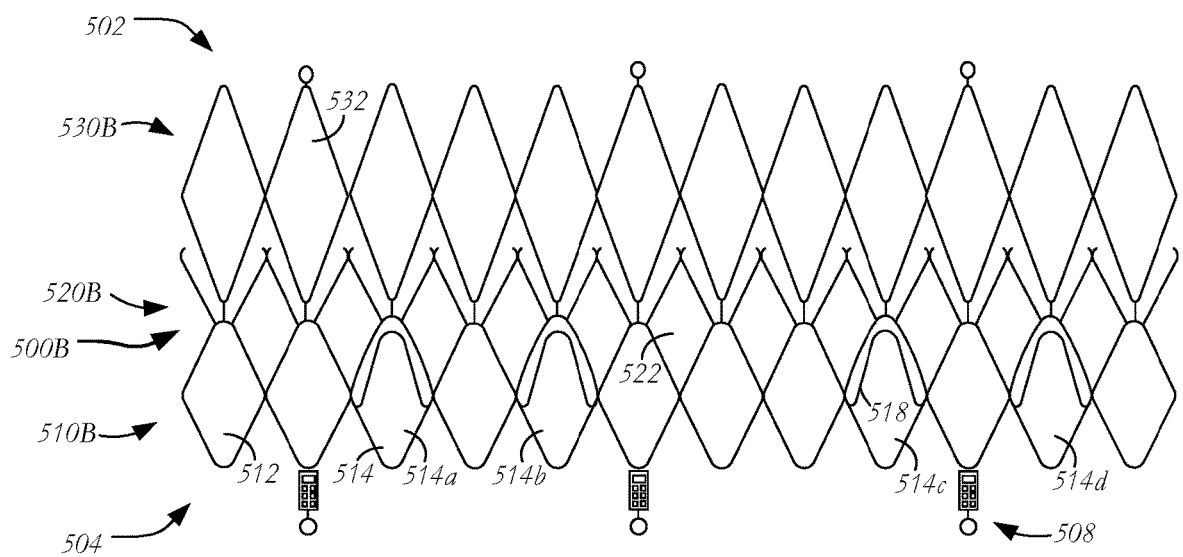
FIG. 5B is a developed view of another example of a stent having a flared portion and a plurality of engaging arms.

FIG. 5B shows a variation in which stent 500B has a twelve-cell configuration (i.e., each row of cells in stent 500B includes twelve cells). Stent 500B extends between inflow end 502 and outflow end 504 and includes a first row of cells 510B having symmetric cells 512 and asymmetric cells 514, a second row of cells 520B having cells 522 and a third row of cells 530B having enlarged cells 532. Engaging arms 518 are nested within two pairs of asymmetric cells 514a, 514b and 514c, 514d, each pair of asymmetric cells being spaced from one another by a symmetric cell. In this example, pairs of engaging arms 518 are offset from one another as much as possible, and provide a generally more symmetric configuration than stent 500A, which allows for simpler coupling of the leaflets. Thus, the positioning of the engaging arms may be affected by the number of cells in the rows of a stent.

Figure 6A:
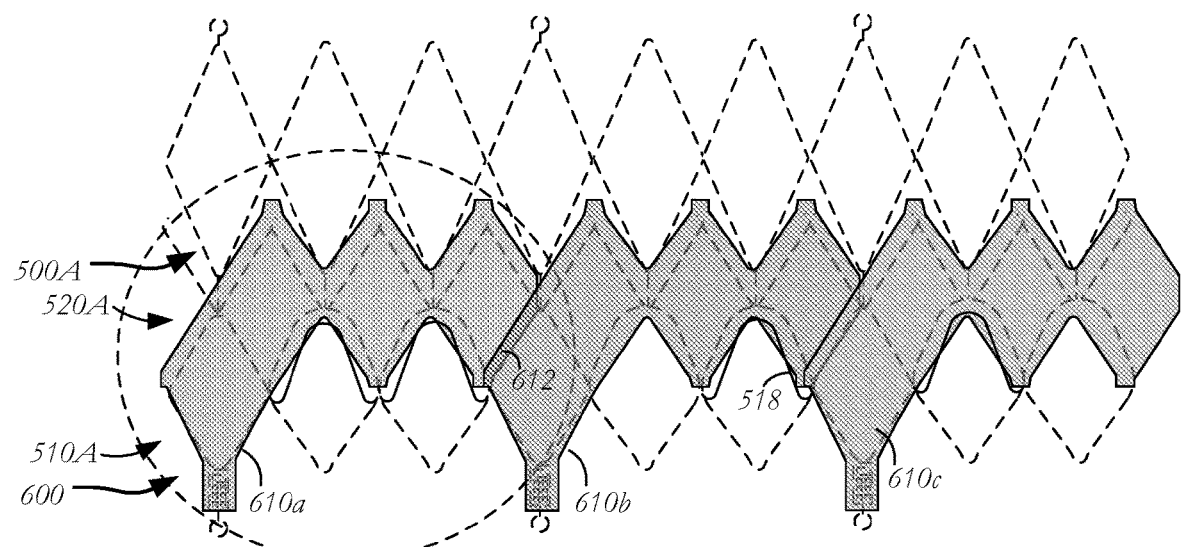
FIGS. 6A and 6B are highly schematic developed views of one example of a cuff configured for coupling to the stent of FIG. 5A.
Figure 6B:
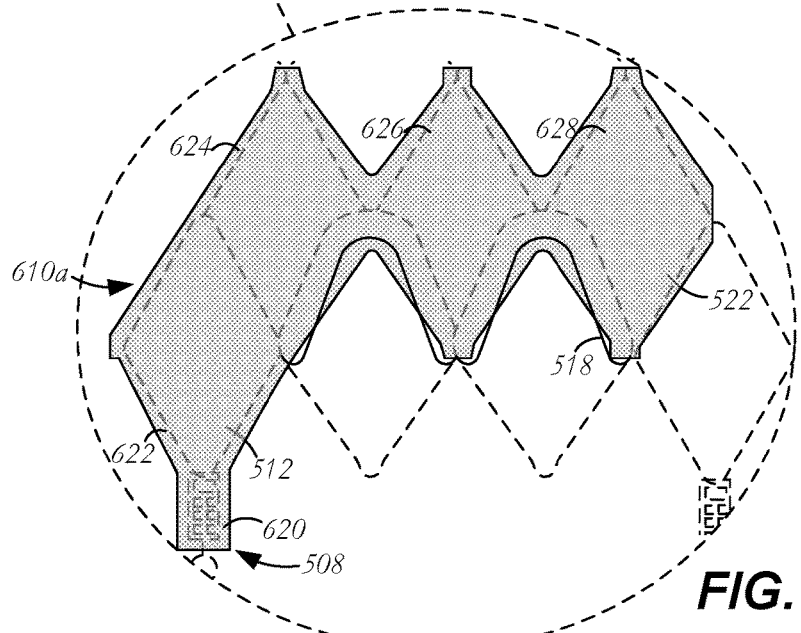

As shown in FIGS. 6A and 6B, a cuff 600 may be disposed over a portion of stent 500A. As illustrated, cuff 600 includes three separate segments 610a-c that are disposed over portions of the first and second rows of cells 510A, 520A and joined together at seams 612. By using a cuff formed of three segments, greater flexibility is provided for making finer adjustments to facilitate the assembly process. FIG. 6B illustrates cuff segment 610a in greater detail, cuff segments 610B and 610c being substantially the same. As shown, cuff segment 610a includes a first portion 620 sized to be disposed over commissure feature 508, a second portion 622 for covering symmetric cell 512 of first row 510A, and three substantially equal third portions 624, 626, 628 for covering three cells 522 of second row 520A. It will be understood that cuff 600 may be disposed on either the luminal or the abluminal surface of stent 500A and that the shape of the cuff may be modified as needed for a stent having a twelve-cell configuration. Additionally, a unitary cuff may be used instead of the three-segmented example shown. When disposed on the abluminal surface of stent 500A, cuff segment 610a may be configured to allow engaging arms 518 to extend therethrough to reach and couple to the native valve leaflets. Thus, engaging arms 518 are preferably unobstructed by cuff 600.

Figure 7A:
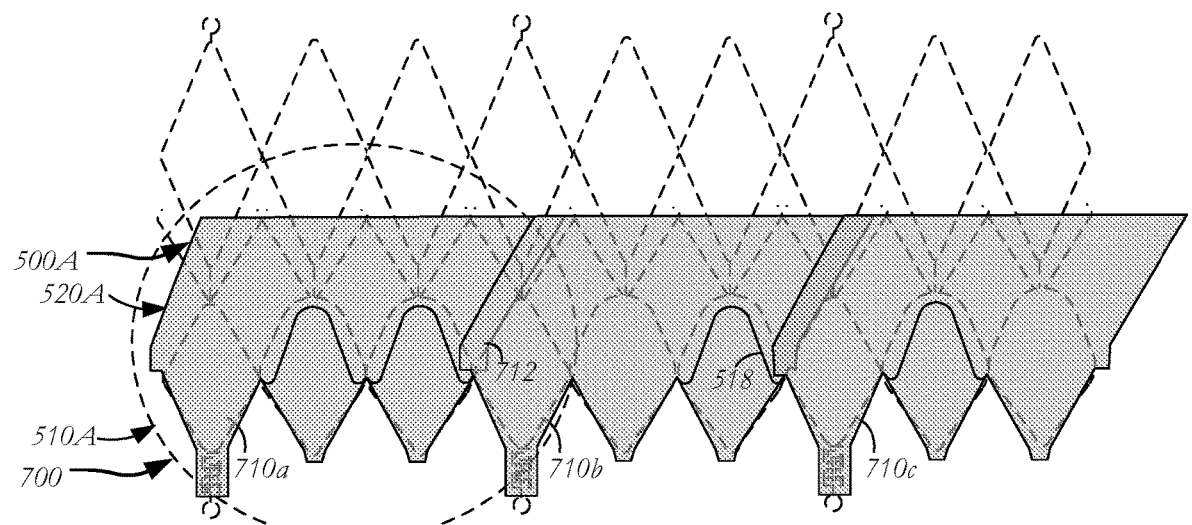
FIGS. 7A and 7B are highly schematic developed views of another example of a cuff configured for coupling to the stent of FIG. 5A.
Figure 7B:
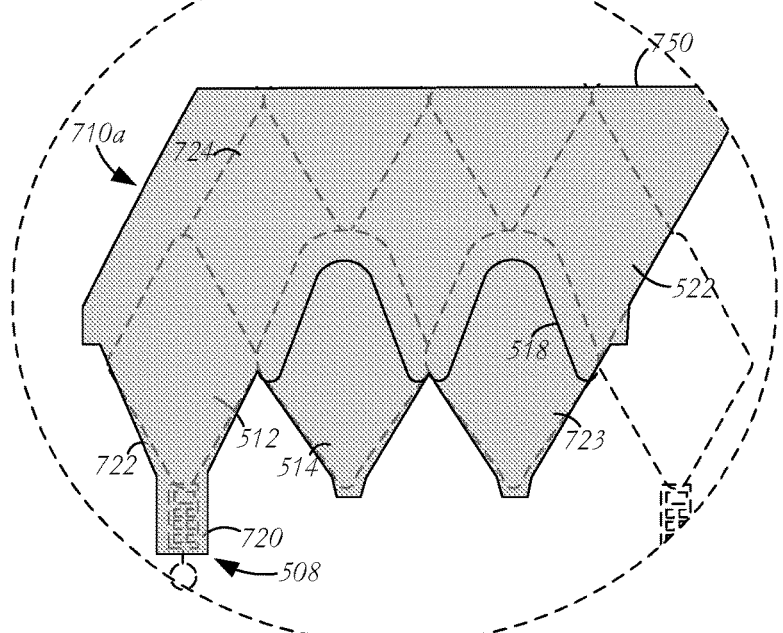

In another variation shown in FIGS. 7A and 7B, cuff 700 may be disposed over a portion of stent 500A. As illustrated, cuff 700 includes three separate segments 710a-c that are disposed over portions of the first and second rows 510A, 520A and joined together at seams 712. The differences between cuff 700 and cuff 600 described above are more readily identifiable by looking at the detailed view of FIG. 7B. As shown, cuff segment 710a includes a first portion 720 sized to be disposed over commissure feature 508. Second portion 722 covers symmetric cell 512 of first row 510A and includes two additional sections 723 for covering asymmetric cells 514. A third portion 724 covers cells 522 of second row 520A and has a substantially straight edge 750 that runs horizontally across the lower corners of cells 532. Cuff 700 is shaped to allow engaging arms 518 to extend over the cuff and couple to the native valve leaflets. Cuff segments 710b and 710c may have the same configuration as cuff segment 710a.

In addition to the cuff, a skirt may be disposed over the third row of cells 530A, 530B to cover flared portion 450 of the stent. FIG. 8 illustrates one example of a skirt 800A configured to cover the third row of cells in a twelve-cell stent configuration (e.g., stent 500B of FIG. 5B). For the sake of clarity, skirt 800A will be described as having multiple portions or components. It will be understood, however, that the skirt may be formed of a single piece of tissue, fabric or polymeric material cut into a predetermined shape and that the portions or components described herein are only indicated for the sake of description and may not be readily discernible from the whole.

As shown, skirt 800A generally includes a hub 802 having a number of sides 803. Hub 802 is shown in the shape of a dodecagon in order to complement a twelve-celled stent. A circular cutout 804 is formed in the center of hub 802 to form void 806 for accepting a portion of the stent. In at least some examples, cutout 804 is formed with a circumference approximately equal to the circumference of a fully expanded stent at the second row of cells. A plurality of quadrilateral tabs 810 extend from the sides of hub 802. In the case of a dodecagon hub, twelve quadrilateral tabs 810 are formed around the perimeter of the hub, one extending from each side 803 of hub 802.

Due to the desired increasing diameter of flared portion 450 of the stent, triangular slits 812 are provided between quadrilateral tabs 810. However, when fully assembled to the stent, edges 811a, 811b of adjacent quadrilateral tabs 810a, 810b will be sewn or otherwise coupled together to close slits 812. Quadrilateral tabs 810 are coupled to one another at seams 830 to form a continuous surface. It will be understood that quadrilateral tabs 810 may be formed such that seams 830 align with struts of stent 500A as shown.

Figure 9A:
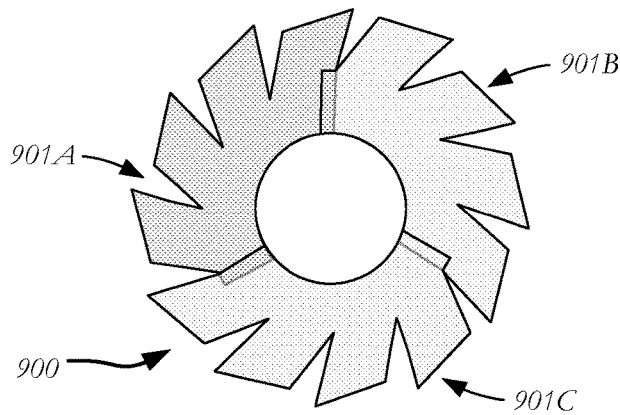
FIGS. 9A-C are highly schematic top views of several variants of a skirt for a prosthetic heart valve.
Figure 9B:
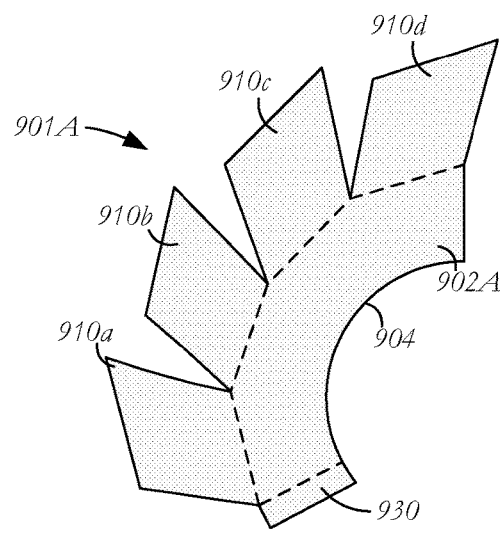
Figure 9C:
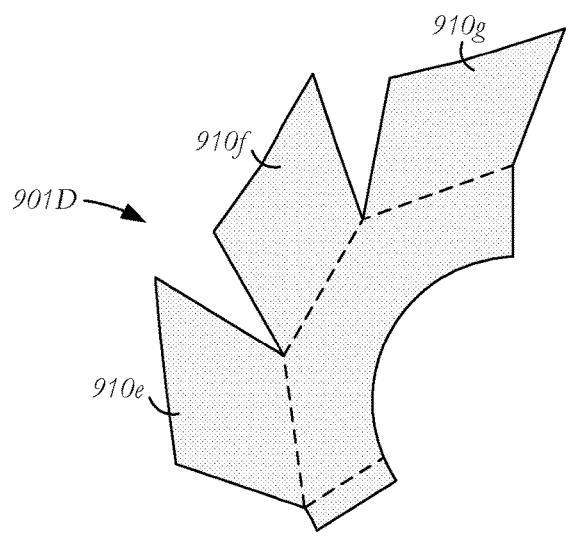

Instead of being formed as a single piece of material, a skirt may be formed in multiple segments. As seen in FIGS. 9A-B, skirt 900 is formed of three equal segments 901A-C. Each of segments 901A-C may include a number of quadrilateral tabs 910a-d extending from a hub portion 902A. It will be understood that each of segments 901A-C may be formed to be substantially the same size and may include the same number of quadrilateral tabs. An optional coupling 930 may be added to each of segments 910A-C and configured to overlap with the hub portion of an adjacent segment to add integrity to the assembly. It will be understood that variations are possible by changing the size and/or shape of the segments. In some variations, the number of quadrilateral tabs may be increased or decreased as desired. For example, as shown in FIG. 9C, a skirt may be formed of three segments 901D, each segment having three quadrilateral tabs 910e-910g.

Figure 10:
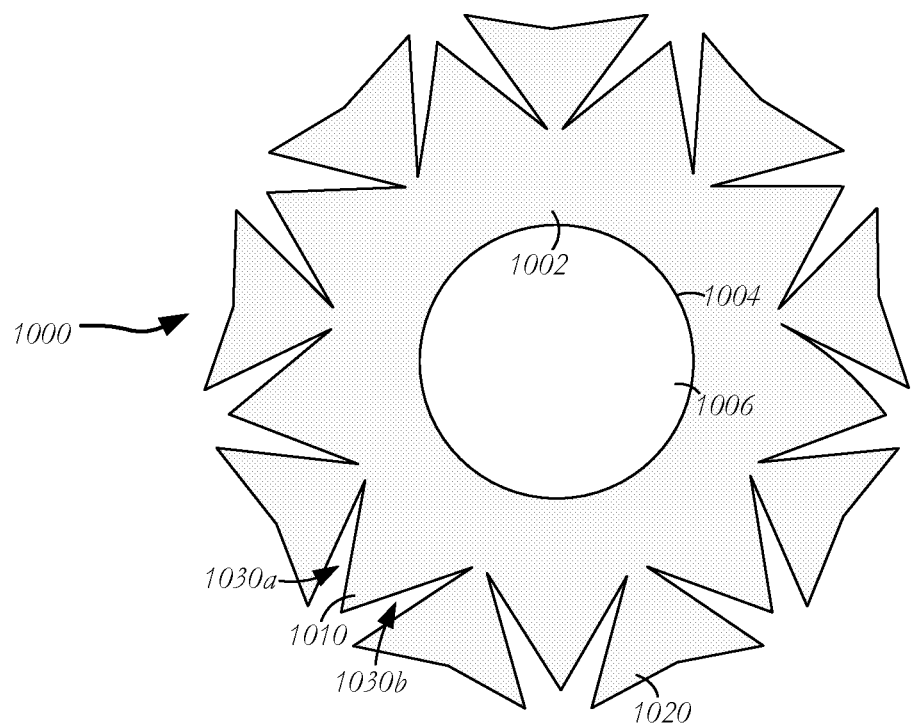
FIG. 10 is a highly schematic top view of another example of a skirt having multiple slits for reduced puckering at the seams.

In another variation, shown in FIG. 10, skirt 1000 includes more slits to reduce puckering at the seams. Similar to skirt 800A, skirt 1000 includes a hub 1002 having circular cutout 1004 at its center to form void 1006 for accepting a portion of the stent. Extending from hub 1002 and disposed on its perimeter are a series of alternating wedges including first wedges 1010 and second wedges 1020. In the examples shown, first wedges 1010 are substantially triangular and are attached at an edge of the triangle to hub 1002, and second wedges 1020 are substantially concave quadrilaterals and are attached to hub 1002 at a point of the triangle. Collectively, wedges 1010 and 1020 define a series of triangles that alternate in their connection to hub 1002. Each first wedge 1010 is disposed between adjacent second wedges 1020 and spaced from the second wedges by slits 1030a, 1030b. When fully assembled, first and second wedges 1010, 1020 adjoin one another at their edges to provide a continuous layer over a row of cells forming a flared portion 450. It will be understood, however, that the shapes of first and second wedges 1010, 1020 may be varied from the shapes shown and described herein and that skirt 1000 may, for example, include a series of wedges in the shape of triangles instead of concave quadrilaterals that are arranged so that each triangle is inverted with respect to an adjacent triangle.

Figure 11:
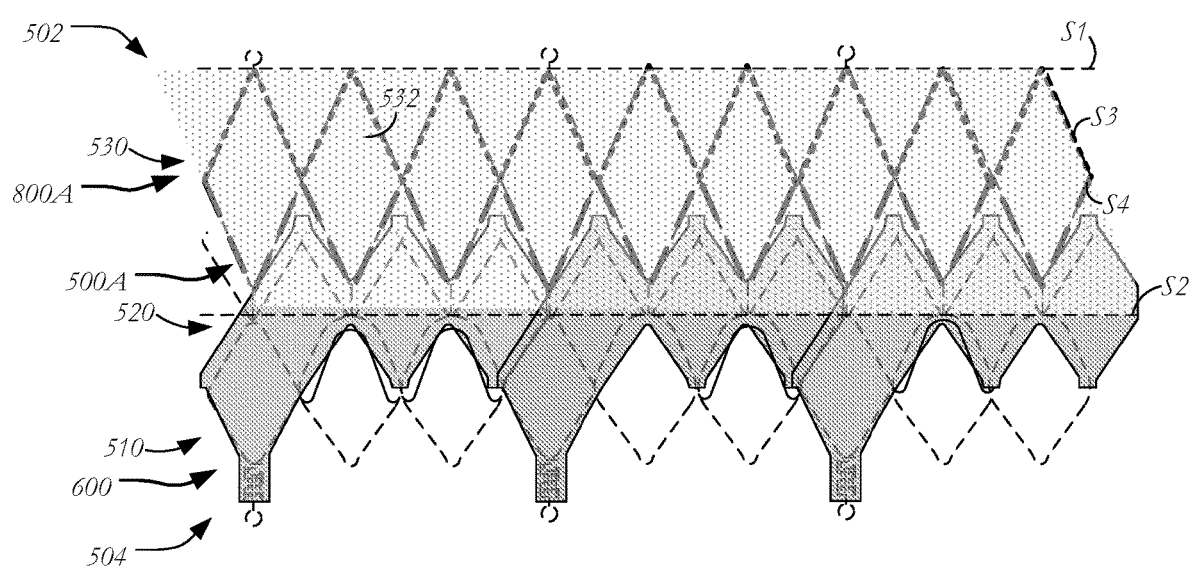
FIG. 11 is a highly schematic developed view of one example of a cuff and a skirt for coupling to a stent having a flared portion and a plurality of engaging arms.

FIG. 11 illustrates one possible suture pattern for attaching a skirt, such as skirt 800A, to stent 500A having cuff 600. A first suture pattern S1 may be formed across the tops of cells 532 in third row of cells 530A at inflow end 502 of stent 500A, and around the circumference of the stent to attach skirt 800A to the stent. A second suture pattern S2 may be formed parallel to the first suture pattern S1 and across the ends of cells 512, 514 in first row of cells 510A and through approximately the midline of cells 522 in second row of cells 520A. A third suture pattern S3 may consist of a zigzag pattern along the struts forming the upper half of enlarged cells 532 of third row of cells 530A, and a fourth suture pattern S4 may form a second zigzag pattern along the struts forming the lower half of enlarged cells 532, the fourth suture pattern S4 being a mirror image of the third suture pattern S3.

Figure 12A:
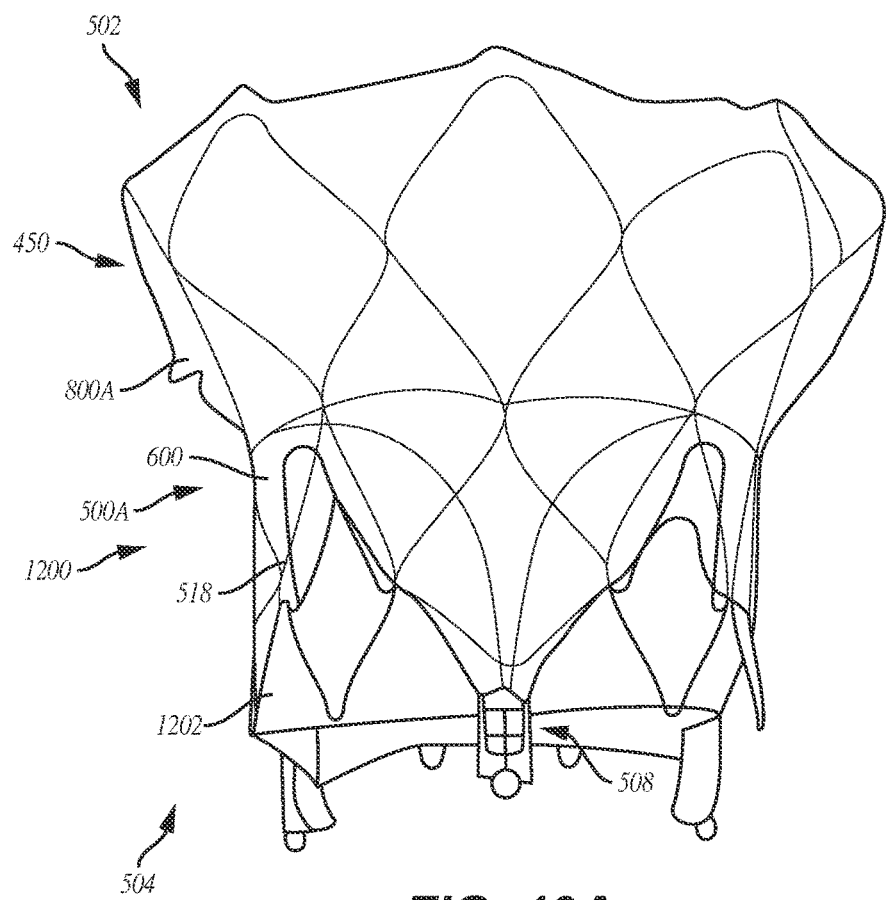
FIGS. 12A-C are photographs showing the side, top and bottom, respectively, of a fully assembled prosthetic heart valve.
Figure 12B:
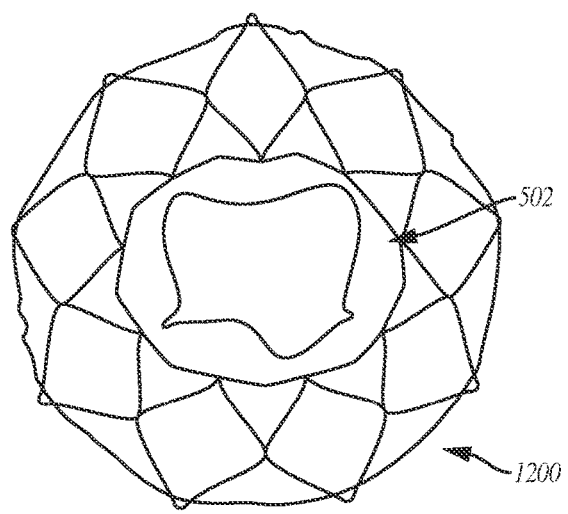
Figure 12C:
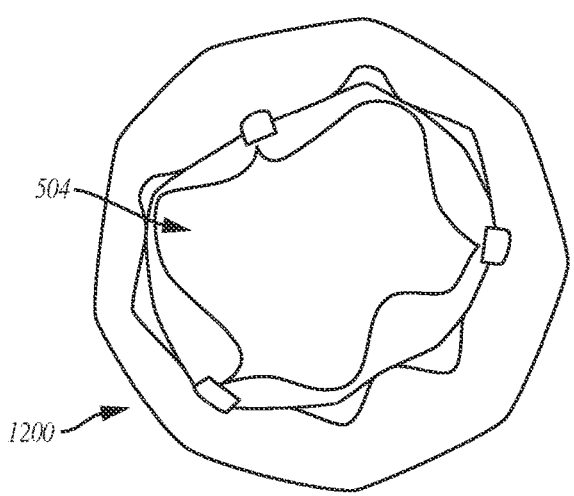

A fully assembled prosthetic heart valve 1200 is shown in FIG. 12A and includes stent 500A having inflow end 502 and outflow end 504. Inflow and outflow end views of prosthetic heart valve 1200 are shown in FIGS. 12B and 12C, respectively. Cuff 600 is disposed on the abluminal surface of a portion of stent 500A adjacent outflow end 504 and skirt 800A is disposed on the abluminal surface of the flared portion 450 of stent 500A adjacent inflow end 502, as described above with reference to FIG. 11. Additionally, three leaflets 1202 have been added to the interior of stent 500A and attached to commissure features 508 and to selected struts of stent 500A and/or to cuff 600 to form a valve assembly as known in the art. Engaging arms 518 may also extend toward inflow end 502 and clip onto, or otherwise couple to, native valve leaflets to aid in anchoring stent 500A to the surrounding tissue. Though cuff 600 covers many cells of stent 500A, engaging arms 518 remain unobstructed to adequately perform their function. When deployed at the mitral valve position, prosthetic heart valve 1200 allows blood flow from atrium 122 to left ventricle 124 and impedes blood backflow from left ventricle 124 to left atrium 122. Flared portion 450 may be disposed at least partially within the native valve annulus and/or left atrium 122 to anchor prosthetic heart valve 1200 (e.g., reduce the possibility of prosthetic heart valve 1200 migrating into left ventricle 124) and/or seal regions around prosthetic heart valve 1200 to reduce paravalvular leakage.

Figure 13:
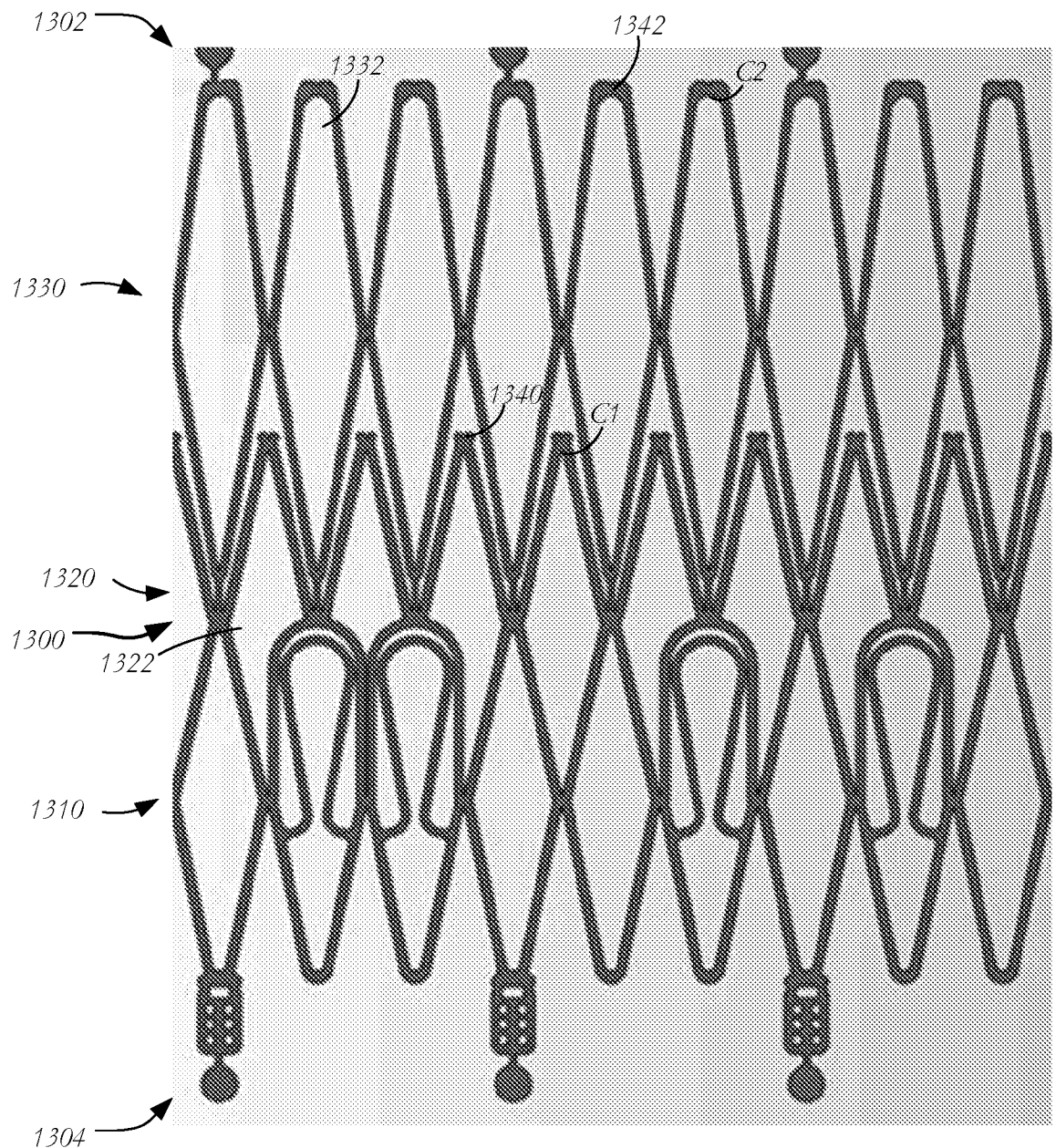
FIG. 13 is a developed view of one example of a stent having multiple horseshoes to aid in suturing.

Several variations of the stent for a prosthetic heart valve are possible. For example, FIG. 13 illustrates stent 1300 extending generally between inflow end 1302 and outflow end 1304 and having three rows of cells 1310, 1320, 1330, similar to the cells of stent 500A described above with reference to FIG. 5A. As shown, each row includes nine cells. The main difference between stent 500A and stent 1300 is the inclusion of horseshoes 1340, 1342 to aid in suturing a cuff and a skirt to stent 1300. Specifically, corners C1 of cells 1322 closest to inflow end 1302 include first horseshoes 1340 to prevent slippage of sutures when coupling a cuff to stent 1300, and corners C2 of enlarged cells 1332 closest to inflow end 1302 include second horseshoes 1342 to prevent slippage of sutures when coupling a skirt to stent 1300.

Figure 14A:
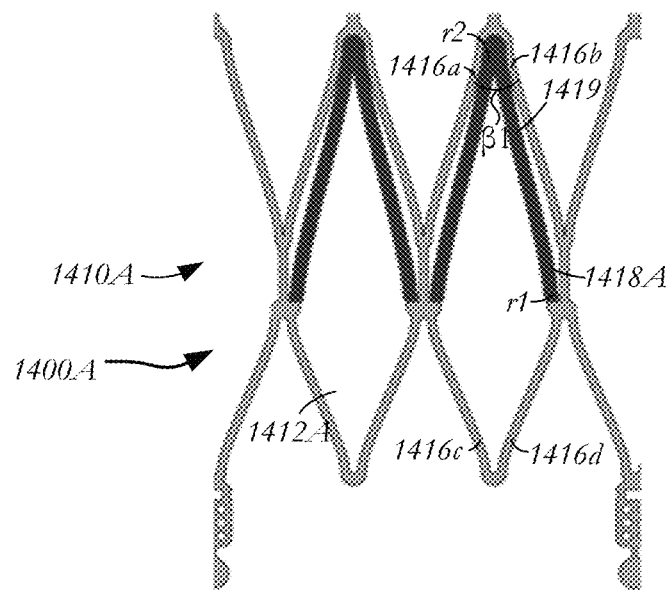
FIGS. 14A and 14B are developed views showing portions of a stent having engaging arms of different shapes.

The shape of the engaging arms may also be modified in several ways. In the simplest configuration, shown in FIG. 14A, stent 1400A includes a first row 1410A of cells 1412A. Each substantially diamond-shaped cell 1412A is composed of four struts 1416a-d joined to one another as shown, struts 1416a and 1416b forming an angle (31 therebetween. Nested engaging arms 1418A are formed of two substantially straight struts 1419 that are coupled to struts 1416c and 1416d at first ends r1 and to each other at second ends r2. Because of the shape of cells 1412A there is little room to form engaging arms 1418A, resulting in a sharp tip at second ends r2 and a tight angle at first ends r1.

Figure 14B:
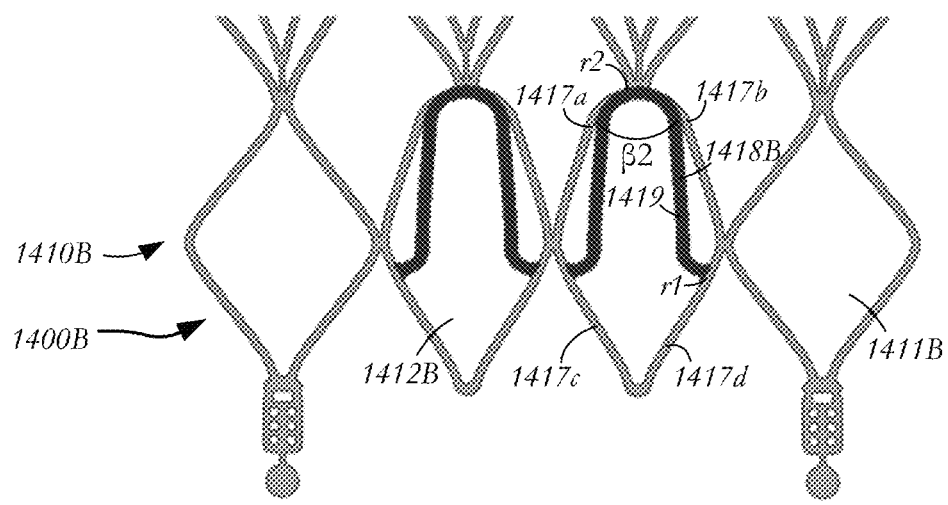

Instead of laser cutting a tube to create a stent in a collapsed state, the tube may be laser cut to create a stent in a partially expanded state. Cutting a stent from a larger diameter tube provides a larger area inside the cells of the stent to form engaging arms. Stent 1400B of FIG. 14B has been formed using this method and generally includes first row of cells 1410B having first cells 1411B and second cells 1412B, second cells 1412B being formed of struts 1417a-d. First cells 1411B that will not include engaging arms may be substantially diamond-shaped, while second cells 1412B that include engaging arms 1418B have a second shape that does not form a diamond. Specifically, struts 1417a and 1417b of cell 1412B may form a slight curvature such that the upper portion of cell 1412B is rounded and forms an angle (32, larger than angle (31, for receiving engaging arms 1418B. With the larger angle (32, an engaging arm 1418B may be formed with a curved loop 1419 having a smooth surface at position r2 that would be less traumatic if brought in contact with body tissue. Additionally, curved loop 1419 includes a wider takeoff at position r1 to reduce or eliminate a pinch point, resulting in less of a stress concentration on the anatomy that is contacted by stent 1400B and easier loading within a delivery device.

As described in the previous examples, engaging arms are not disposed within each cell of first row 1410B. Thus, in forming a stent having engaging arms, the various features of stent 1400B may be cut from a metal tube under different conditions. For example, cells 1411B that do not have engaging arms 1418B may be cut when the tube is in a radially collapsed condition, and cells that include engaging arms 1418B may be cut when the tube is in a partially expanded condition. This approach avoids the need for cutting stent 1400B out of a large diameter tube as the large diameter tube can be expensive and more difficult to manufacture. Selectively cutting portions in the collapsed and partially expanded conditions allows for manufacturing the configurations shown out of a relatively small diameter tube.

Figure 15:
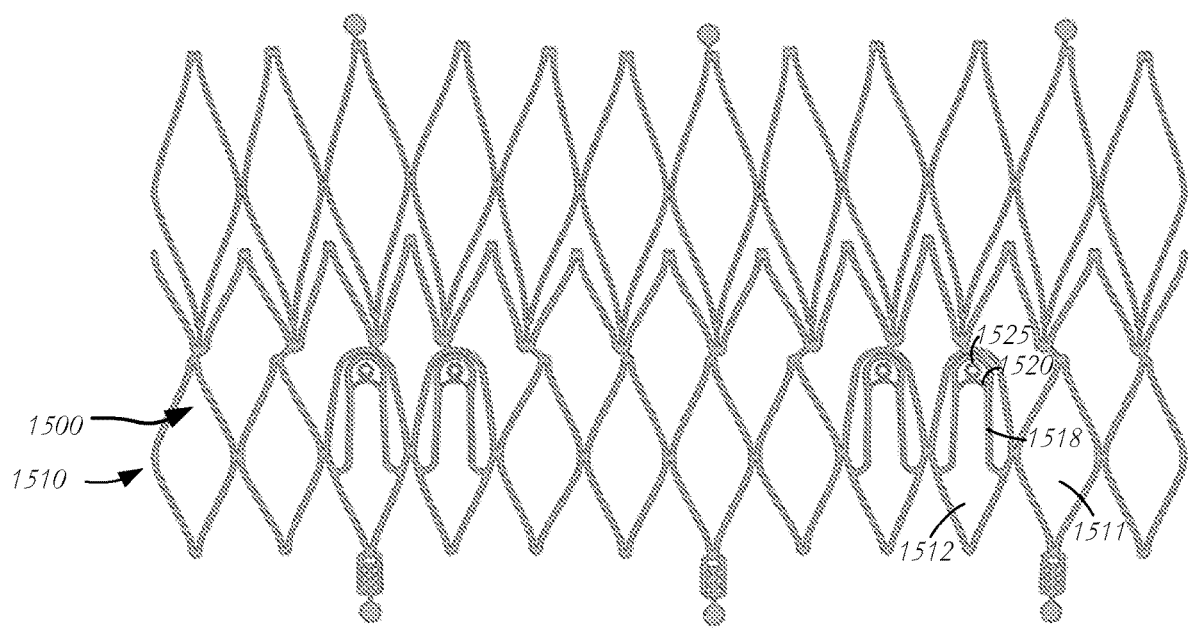
FIG. 15 is a developed view of one example of a stent having circular supports for accepting radiopaque markers.

In another variation shown in FIG. 15, stent 1500 may include features to aid in visualization during deployment. Stent 1500 may be substantially similar to stent 500A described above, and may include a first row 1510 of cells having first cells 1511 and second cells 1512, second cells 1512 including engaging arms 1518 therein. The main difference between stent 1500 and stent 500A is the presence of a bridging strut 1520 extending between the struts forming each engaging arm 1518 as shown. Bridging struts 1520 include a circular support 1525 for accepting a radiopaque marker (e.g., tantalum markers) to help make engaging arms 1518 more visible under fluoroscopy and/or echocardiography. Thus, the orientation of stent 1500 with respect to the native valve annulus may be more accurately detected so that engaging arms 1518 may be aligned with the native valve leaflets.

Additional variations in the configurations of the stents are possible. For example, the stent may optionally include a braided material in a variety of configurations. These braided portions may be combined in various manners with any of the stents and cuffs previously described or with variations of the engaging arms as will be discussed below. Thus, the teachings of the present disclosure are not independent and various features may be combined to achieve one or more benefits, such as reduced paravalvular leakage, better anchoring, a better crimp profile and the like.

For example, as previously described with reference to FIG. 3, a prosthetic heart valve may be formed with a frame of braided material surrounding the stent to reduce paravalvular leakage by engaging tissue and filling spaces between the prosthetic valve and the native valve annulus. In addition to what has been already described, the braided material may be disposed on the stent in various other configurations. Two such variations are shown in FIGS. 16A-D. Though the valve assembly including the cuff and leaflets are not shown, it will be understood that any of the variations described above for forming the valve assembly may be combined with the stents and frames of FIGS. 16A-D.

As shown in FIG. 16A, a stent 1601 for a prosthetic heart valve has an inflow end 1602, an outflow end 1604 and a plurality of struts 1605 forming one or more rows of cells 1610. Stent 1601 includes a number of engaging arms 1618 similar to engaging arms 1518, each engaging arm having a bridging strut 1620 and a circular eyelet 1625 formed by a loop in the bridging strut 1620. One noteworthy feature of this variation is the use of a braided crown 1630 at inflow end 1602 of stent 1601. In this example, braided crown 1630 is formed of any of the mesh-like materials or configurations described above with reference to FIG. 3, and extends generally perpendicular to the longitudinal axis y of stent 1601, flaring radially outward a distance d1 of between about 5 mm and about 15 mm from struts 1605 of stent 1601 in the expanded condition.

As shown, stent 1601 includes a single full row of cells 1610, engaging arms 1618 being coupled to selected cells. Engaging arms 1618 are tilted at an oblique angle to the longitudinal axis, a feature that will be described in more detail below with reference to FIGS. 18A-B. Braided crown 1630 is attached to stent 1601 via a plurality of connectors 1635, the braided material being crimped together at each connector and coupled to a strut of the stent. In the example shown, a single connector 1635 is disposed above each cell 1610 such that in a nine-cell stent nine connectors 1635 are provided. It will be understood that more or less connectors 1635 may be provided. For example, connectors 1635 may skip one or more cells. In at least some examples, braided material is crimped over itself and joined to the stent via welding, adhesive or other suitable techniques, connector 1635 being optionally cylindrical and disposed over the braided material and a strut of the stent.

FIG. 16B is a schematic representation showing the general profile of braided crown 1630. Braided crown 1630 generally includes vertical portions 1641 coupled to stent 1601 at the connectors as discussed, a horizontal portion 1643 disposed generally perpendicular to vertical portions 1641, and a transition curvature 1642 between the vertical portion and the horizontal portion. In use, stent 1601 may be at least partially disposed the within native valve annulus while braided crown 1630 may be disposed within the left atrium, the flared horizontal portion 1643 providing anchoring for the prosthetic heart valve so that the valve is incapable of migrating into the left ventricle.

In another variation, shown in an expanded condition in FIG. 16C, a stent 1651 for a prosthetic heart valve has an inflow end 1652, an outflow end 1654 and a plurality of struts 1655 forming two rows of generally diamond-shaped cells 1660, 1661. Specifically, a lower row of cells 1660 is disposed adjacent outflow end 1654 and is joined to an upper row of cells 1661 disposed adjacent inflow end 1652, each cell 1661 of the upper row being defined by two struts 1665a, 1665b that are shared with the lower cells and two additional struts 1665c, 1665d (FIG. 16D). The upper and lower struts in upper cells 1661 are coupled together at junctions 1667, which coincide with the peaks of the lower cells 1660. Stent 1651 also includes a number of engaging arms 1668 similar to engaging arms 1618, each engaging arm having a bridging strut 1670 and a circular eyelet 1675 formed by a loop in the bridging strut 1670. In this example, braided crown 1680 is disposed adjacent inflow end 1652 of stent 1651, portions of the braided wires being attached to stent 1651 with connectors 1685 at junctions 1667 via any of the methods described above with respect to FIGS. 16A-B.

Braided crown 1680 extends initially from connectors 1685 toward inflow end 1652 then bends over itself toward outflow end 1654. The general profile of braided crown 1680 is shown in FIG. 16E. In use, stent 1651 including most of lower cells 1660 may be disposed within the native valve annulus while upper cells 1661 may extend into the left atrium, braided crown 1680 also being disposed within the left atrium to provide anchoring for the prosthetic heart valve so that the valve is incapable of migrating into the left ventricle.

As briefly mentioned, the engaging arms may also be constructed in several ways to provide additional benefits. Two additional examples of engaging arms will now be described, which may be used with any of the stent examples discussed above. In FIGS. 17A-G, one example of an engaging arm known as a teeter-totter arm is shown. As shown in FIGS. 17A, stent 1700 extends between inflow end 1702 and outflow end 1704 and includes a braided crown 1705, similar to crown 1680 and a plurality of engaging arms 1710.

A more detailed view of a single engaging arm 1710 is shown in FIG. 17B. Engaging arm 1710 is nested within cell 1712, which is generally formed by two upper struts 1713a, 1713*b* and two lower struts 1713*c*, 1713*d*. Although generally diamond-shaped cells are described, it will be understood that variations of the cell shape are contemplated and that terms such as "apex" and "corner" used herein are not to be taken narrowly as forming an angle, but rather as a position where two struts meet. Thus, struts may meet one another at apices or corners that have a curvature.

Engaging arm 1710 includes two connecting portions 1715 joined to lower struts 1713*c*, 1713*d*, respectively, at junctions 1714, and two generally parallel, longitudinally-extending struts 1716, which are joined together at rounded end 1718. Connecting portions 1715 space engaging arm 1710 from the struts forming cell 1712. Junctions 1714 may be disposed along lower struts 1713*c*, 1713*d* at a distance x1 from corners 1717, at which lower struts 1713*c*, 1713*d* are connected to upper struts 1713*a*, 1713*b*, respectively. In one example, distance x1 is closer to corners 1717 than to the lower apex 1711 of the cell (e.g., between approximately one-quarter and one-third of the length of lower struts 1713*c*, 1713*d*). Bridging strut 1719 forming central eyelet 1720 extends between longitudinally-extending struts 1716 as described in earlier examples.

As will be appreciated from the figures, the joining of engaging arm 1710 to the lower struts 1713*c*, 1713*d* allows engaging arm 1710 to move in response to the movement of lower struts 1713*c*, 1713*d*. This synchronous movement of the engaging arms 1710 and the lower struts is shown in FIGS. 17C-F. As shown in FIG. 17C, in a relaxed condition both engaging arm 1710 and lower struts 1713*c*, 1713*d* may be biased radially outward with respect to a longitudinal direction w1 of the stent. Specifically, in the relaxed condition, engaging arm 1710 may be joined to lower struts 1713*c*, 1713*d* at a fixed angle a1 of between about 90 degrees and about 170 degrees. In the relaxed condition shown in FIG. 17C, engaging arm 1710 may form a second angle a2 of between about 5 degrees and about 85 degrees with respect to the longitudinal direction w1 of the stent. Also in the relaxed condition, lower struts 1713*c*, 1713*d* may form a third angle a3 of between about 5 degrees and about 85 degrees with the longitudinal direction w1 of the stent.

Applying a force f1 on lower struts 1713*c*, 1713*d* radially inward toward the center of the device causes the struts to pivot at corners 1717. This pivoting of struts 1713*c*, 1713*d* radially inward result in a commensurate movement of engaging arm 1710 radially outward (FIG. 17D). When lower struts 1713*c*, 1713*d* are pressed until they are parallel with longitudinal direction w1, angle a3 becomes zero, and angle a2 is the sum of angles a2 and a3 in the relaxed condition. In some examples, angle a1 may remain substantially the same as in the relaxed configuration. Releasing lower struts 1713*c*, 1713*d* causes them to travel radially outward to the relaxed condition shown in FIG. 17C and engaging arm 1710 to travel radially inward also to the relaxed condition.

The synchronous movement of lower struts 1713*c*, 1713*d* and engaging arm 1710 may be useful during delivery of a prosthetic heart valve as shown in FIGS. 17E-G. In FIG. 17E, stent 1700 is in a loaded condition within delivery sheath 1750, engaging arms 1710 and struts 1713*c*, 1713*d* being parallel with the longitudinal direction w1 of stent 1700. To release the device, delivery sheath 1750 is retracted in the direction of arrow b1 toward the outflow end of the stent (not shown), while stent 1700 remains fixed or is urged forward. As shown in FIG. 17F, in a partially-released condition in which sheath 1750 uncovers, engaging arms 1710 (i.e., as the free end of the sheath approach junctions 1714), the exposed portion of each engaging arm 1710 deflects outwardly to an angle a2 of approximately 45 degrees, while the lower struts (not shown) are still constrained within delivery sheath 1750. This allows engaging arm 1710 to flare outwardly at a wide angle to capture the native valve leaflet in the enlarged cavity 1770 between engaging arm 1710 and the rest of stent 1700. Once the native valve leaflet is positioned within cavity 1770, delivery sheath 1750 may be further retracted in direction b1 to a fully-released (e.g., relaxed) condition to liberate lower struts 1713*c*, 1713*d*, causing both the lower struts and the engaging arm 1710 to return to their relaxed condition, whereby angle a2 is reduced to approximately 30 degrees, grasping the native valve leaflet within cavity 1770.

Figure 18A:
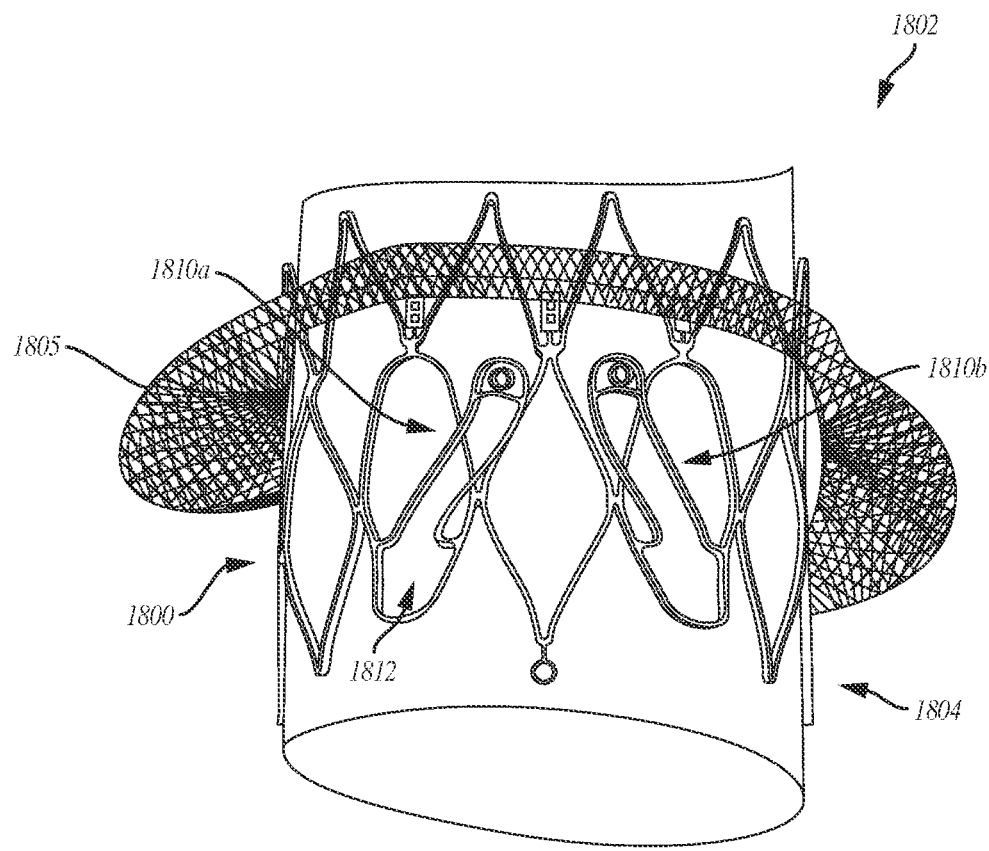
FIGS. 18A-C are photographs and schematic representations of a variation of a stent having criss-crossing engaging arms.

Additionally, or in the alternative, the engaging arms may be heat-set so as to be inclined toward one another to aid in visualization during deployment. As shown in FIG. 18A, stent 1800 extends between inflow end 1802 and outflow end 1804 and includes a braided crown 1805, similar to crown 1680 discussed above, and one or more pairs of engaging arms 1810*a*, 1810*b*. Engaging arms 1810*a*, 1810*b* are not fully nested within cells 1812, but are heat-set to slope diagonally toward one another.

Figure 18B:
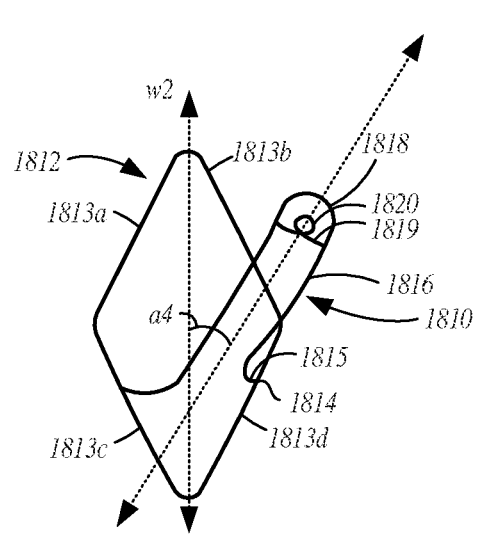

A more detailed view of a single engaging arm 1810 is shown in FIG. 18B. Engaging arm 1810 is connected to cell 1812, which is generally formed by two upper struts 1813*a*, 1813*b* and two lower struts 1813*c*, 1813*d*. Engaging arm 1810 includes two connecting portions 1815 joined to lower struts 1813*c*, 1813*d*, respectively, at junctions 1814 and two generally parallel, longitudinally-extending struts 1816, which are joined together at rounded end 1818. Bridging strut 1819 forming central eyelet 1820 extends between longitudinally-extending struts 1816. Engaging arm 1810 may be heat-set so that, in the relaxed condition, engaging arm 1810 slopes at an angle a4 of between about 5 degrees and about 80 degrees with respect to a longitudinal axis w2 of cell 1812.

Figure 18C:
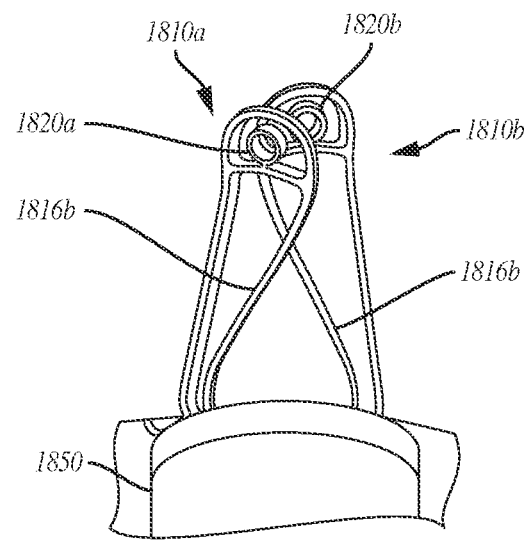

When disposed within a delivery sheath 1850, engaging arms 1810*a*, 1810*b* may at least partially overlap with one another during deployment (FIG. 18C). In some examples, the extent of the overlap of engaging arms 1810*a*, 1810*b* may result in circular eyelets 1820*a*, 1820*b* being directly aligned with one another. In another example, the extent of the overlap of engaging arms 1810*a*, 1810*b* may result in an overlap of at least the two directly opposed longitudinal struts 1816*b* of respective engaging arms. It will be understood that a stent may have several pairs of engaging arms (e.g., two pairs of engaging arms or three pairs of engaging arms) and that each engaging arm may crisscross with a complementary engaging arm. As engaging arms 1810 are released, they travel further apart until the stent takes the shape shown in FIG. 18A.

In some embodiments, a prosthetic heart valve has an inflow end, an outflow end and a longitudinal axis extending from the inflow end to the outflow end and includes a collapsible and expandable stent including a plurality of cells arranged in at least one row extending around a circumference of the stent. The stent further includes at least one engaging arm joined to one of the cells adjacent the outflow end and having a free end extending toward the inflow end, the engaging arm being movable between a loaded condition in which the engaging arm is oriented substantially parallel with the longitudinal axis of the stent, a partially-released condition in which the engaging arm forms a first angle with the longitudinal axis of the stent, and a fully-released condition in which the engaging arm forms a second angle with the longitudinal axis of the stent, the first angle being larger than the second angle. A collapsible and expandable valve assembly is disposed within the stent and having a plurality of leaflets.

In some examples, the at least one engaging arms may include two engaging arms for coupling to each native valve leaflet at a site of implantation; and/or the engaging arm may include two longitudinally-extending struts coupled together at a rounded end; and/or the engaging arm further may include a bridging strut interconnected between the two longitudinally-extending struts, the bridging strut including a loop defining an eyelet; and/or the engaging arm may be nested within the one cell, the one cell having two upper struts joined to one another at an upper apex, two lower struts joined one another at a lower apex, the lower struts being joined to the upper struts at corners, the engaging arm being joined to the lower struts of the one cell; and/or a rotation of the lower struts may cause a complementary rotation of the engaging arm; and/or the engaging arm may be joined to the lower struts at locations along lengths of the lower struts, the locations being closer to the corners than to the lower apex; and/or in the fully-released condition, the engaging arm may form an angle of between about 90 degrees and about 170 degrees with the lower struts; and/or in the fully-released condition, the lower struts may form an angle of between about 5 degrees and about 85 degrees with the longitudinal axis of the stent; and/or the first angle may be between about 40 and about 50 degrees, and the second angle may be between about 30 and about 40 degrees; and/or the prosthetic heart valve may be a mitral valve.

In some embodiments, a prosthetic heart valve has an inflow end and an outflow end, and may include a collapsible and expandable stent including a plurality of cells arranged in at least one row extending around a circumference of the stent. The stent further includes at least one engaging arm joined to one of the cells adjacent the outflow end and having a free end extending toward the inflow end, the engaging arm being connected to a selected cell, the one cell having two upper struts joined to one another at an upper apex, two lower struts joined one another at a lower apex, the lower struts being joined to the upper struts at corners, the engaging arm being joined to the lower struts of the one cell and movable between a loaded condition and a relaxed condition, the engaging arm being sloped with respect to a longitudinal axis of the one cell in the relaxed condition. A collapsible and expandable valve assembly may be disposed within the stent and having a plurality of leaflets.

In some examples, the engaging arm may be heat-set to form an angle of between about 5 degrees and about 85 degrees with respect to the longitudinal axis of the selected cell; and/or the at least one engaging arm may include two complementary engaging arms for coupling to each native valve leaflet at a site of implantation, the complementary engaging arms being sloped toward one another in the relaxed condition; and/or the at least one engaging arm may include two complementary engaging arms for coupling to each native valve leaflet at a site of implantation, the complementary engaging arms being at least partially overlapped with one another in the relaxed condition; and/or the prosthetic heart valve may be a mitral valve.

In some embodiments, a method of delivering a prosthetic heart valve may include providing a collapsible and expandable valve assembly and a collapsible and expandable stent having an inflow end, an outflow end, and a longitudinal axis extending from the inflow end to the outflow end, the stent including a plurality of cells arranged in at least one row, each row extending around a circumference of the stent, the stent further including at least one engaging arm joined to one of the cells adjacent the outflow end and having a free end extending toward the inflow end, the one cell having two upper struts joined to one another at an upper apex, two lower struts joined one another at a lower apex, the lower struts being joined to the upper struts at corners, the engaging arm being joined to the lower struts of the one cell. The stent and valve assembly may be loaded within a delivery sheath, and the delivery sheath may be advanced to a patient's native valve annulus.

In some examples, the delivery sheath may be retracted a first distance away from the inflow end of the stent to release the engaging arm so that the engaging arm forms a first angle with respect to the longitudinal axis of the stent; and/or the delivery sheath may be retracted an additional distance away from the inflow end of the stent to release the lower struts so that the at engaging arm forms a second angle with respect to the longitudinal axis of the stent, the second angle being less than the first angle; and/or the method may include the step of releasing the delivery sheath from the stent and removing the delivery sheath from the body.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve, comprising:
    a collapsible and expandable stent extending along a longitudinal axis and having an inflow end and an outflow end, the stent including a plurality of cells annularly arranged around the stent in at least one row, the plurality of cells having a first nesting cell adjacent the outflow end of the stent, the first nesting cell having two upper struts joined together at an upper apex, two lower struts joined together at a lower apex, and corners joining the two upper struts to the two lower struts;
    a first engaging arm disposed within the first nesting cell and being pivotally movable between a loaded condition, a partially-released condition, and a fully-released condition, the first engaging arm being joined to the two lower struts of the first nesting cell at locations away from the corners so that the first engaging arm and the first nesting cell have a synchronous pivoting movement; and
    a collapsible and expandable valve assembly disposed within the stent and having a plurality of leaflets.

2. The prosthetic heart valve of claim 1, wherein the first engaging arm has a free end extending toward the inflow end of the stent.

3. The prosthetic heart valve of claim 1, wherein the first engaging arm is transitionable between the loaded condition in which the first engaging arm is oriented parallel with the longitudinal axis of the stent, the partially-released condition in which the first engaging arm extends radially outward from the stent to form a first angle with the longitudinal axis of the stent, and the fully-released condition in which the first engaging arm extends radially outward from the stent to form a second angle with the longitudinal axis of the stent, the first angle being larger than the second angle.

4. The prosthetic heart valve of claim 3, wherein the first angle is between 40 and 50 degrees, and the second angle is between 30 and 40 degrees.

5. The prosthetic heart valve of claim 1, wherein the first engaging arm includes two longitudinally-extending struts coupled together at a rounded end.

6. The prosthetic heart valve of claim 5, wherein the first engaging arm further comprises a bridging strut interconnected between the two longitudinally-extending struts, the bridging strut including a loop defining an eyelet.

7. The prosthetic heart valve of claim 1, wherein a rotation of the lower struts causes a complementary rotation of the first engaging arm.

8. The prosthetic heart valve of claim 1, wherein the first engaging arm is joined to the lower struts at locations along a length of the lower struts, the locations being closer to the corners than to the lower apex.

9. The prosthetic heart valve of claim 1, wherein, when the first engaging arm is in the fully-released condition, the first engaging arm forms an angle of between 90 degrees and 170 degrees with the lower struts.

10. The prosthetic heart valve of claim 1, wherein, when the first engaging arm is in the fully-released condition, the lower struts form an angle of between 5 degrees and 85 degrees with the longitudinal axis of the stent.

11. The prosthetic heart valve of claim 1, wherein the stent includes a second nesting cell and a second engaging arm disposed within the second nesting cell.

12. The prosthetic heart valve of claim 11, wherein the first nesting cell and the second nesting cell are disposed on a same side of the stent.

13. The prosthetic heart valve of claim 1, further comprising a braided crown disposed adjacent the inflow end of the stent.

14. The prosthetic heart valve of claim 13, wherein the braided crown extends perpendicular to the longitudinal axis of the stent.

15. The prosthetic heart valve of claim 13, wherein the braided crown extends toward the outflow end of the stent.

16. The prosthetic heart valve of claim 1, wherein the prosthetic heart valve is a prosthetic mitral valve.

17. The prosthetic heart valve of claim 1, wherein the first engaging arm is joined to the first nesting cell at only two locations.

* * * * *